(12) United States Patent
Chung et al.

(10) Patent No.: US 9,993,149 B2
(45) Date of Patent: Jun. 12, 2018

(54) FOURIER PTYCHOGRAPHIC RETINAL IMAGING METHODS AND SYSTEMS

(71) Applicant: California Institute of Technology, Pasadena, CA (US)

(72) Inventors: Jaebum Chung, Pasadena, CA (US); Roarke W. Horstmeyer, Palo Alto, CA (US); Changhuei Yang, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days. days.

(21) Appl. No.: 15/081,659

(22) Filed: Mar. 25, 2016

(65) Prior Publication Data

US 2017/0273551 A1    Sep. 28, 2017

Related U.S. Application Data

(60) Provisional application No. 62/137,955, filed on Mar. 25, 2015.

(51) Int. Cl.
| | |
|---|---|
| *A61B 3/14* | (2006.01) |
| *A61B 3/00* | (2006.01) |
| *A61B 3/12* | (2006.01) |
| *G02B 26/08* | (2006.01) |
| *G02B 26/02* | (2006.01) |

(Continued)

(52) U.S. Cl.
CPC .............. *A61B 3/0025* (2013.01); *A61B 3/12* (2013.01); *A61B 3/14* (2013.01); *G02B 26/02* (2013.01); *G02B 26/0833* (2013.01); *G06T 7/0012* (2013.01); *G06T 11/003* (2013.01); *G06T 2207/10004* (2013.01); *G06T 2207/30041* (2013.01)

(58) Field of Classification Search
CPC ........... A61B 3/0025; A61B 3/14; A61B 3/12; G02B 26/0833; G02B 26/02; G06T 11/003; G06T 7/0012; G06T 2207/30041; G06T 2207/10004
USPC ........................................ 351/206, 205, 200
See application file for complete search history.

(56) References Cited

U.S. PATENT DOCUMENTS

| | | | |
|---|---|---|---|
| 5,475,527 | A | 12/1995 | Hackel et al. |
| 6,144,365 | A | 11/2000 | Young et al. |
| 6,154,196 | A | 11/2000 | Fleck et al. |

(Continued)

FOREIGN PATENT DOCUMENTS

| | | |
|---|---|---|
| CN | 101408623 A | 4/2009 |
| CN | 101868740 A | 10/2010 |

(Continued)

OTHER PUBLICATIONS

U.S. Appl. No. 15/068,389, filed Mar. 11, 2016 entitled "Correcting for Aberrations in Incoherent Imaging Systems Using Fourier Ptychographic Techniques".

(Continued)

*Primary Examiner* — Tuyen Tra
(74) *Attorney, Agent, or Firm* — Sheila Martinez-Lemke; Weaver Austin Villeneuve & Sampson LLP

(57) ABSTRACT

Certain embodiments pertain to Fourier ptychographic retinal imaging methods and systems that focus on a retina of an eye to acquire a sequence of raw retinal images, construct a full-resolution, complex retinal image from the sequence of raw retinal image and correct the aberration in the full-resolution, complex retinal image to generate a substantially aberration-free retinal image.

21 Claims, 7 Drawing Sheets

(51) Int. Cl.
  *G06T 11/00* (2006.01)
  *G06T 7/00* (2017.01)

(56) References Cited

U.S. PATENT DOCUMENTS

| | | | |
|---|---|---|---|
| 6,320,648 B1 | 11/2001 | Brueck et al. |
| 6,747,781 B2 | 6/2004 | Trisnadi |
| 6,905,838 B1 | 6/2005 | Bittner |
| 7,436,503 B1 | 10/2008 | Chen et al. |
| 7,460,248 B2 | 12/2008 | Kurtz et al. |
| 7,706,419 B2 | 4/2010 | Wang et al. |
| 7,787,588 B1 | 8/2010 | Yun et al. |
| 8,271,251 B2 | 9/2012 | Schwartz et al. |
| 8,313,031 B2 | 11/2012 | Vinogradov |
| 8,497,934 B2 | 7/2013 | Milnes et al. |
| 8,624,968 B1 | 1/2014 | Zheng et al. |
| 8,942,449 B2 | 1/2015 | Maiden |
| 9,029,745 B2 | 5/2015 | Maiden |
| 9,426,455 B2 | 8/2016 | Horstmeyer et al. |
| 9,497,379 B2 | 11/2016 | Ou et al. |
| 9,829,695 B2 | 11/2017 | Kim et al. |
| 9,864,184 B2 | 1/2018 | Ou et al. |
| 9,892,812 B2 | 2/2018 | Zheng et al. |
| 2001/0055062 A1 | 12/2001 | Shioda et al. |
| 2002/0141051 A1 | 10/2002 | Vogt et al. |
| 2003/0116436 A1 | 6/2003 | Amirkhanian et al. |
| 2004/0146196 A1 | 7/2004 | Van Heel |
| 2004/0190762 A1 | 9/2004 | Dowski, Jr. et al. |
| 2005/0211912 A1 | 9/2005 | Fox |
| 2006/0098293 A1 | 5/2006 | Garoutte et al. |
| 2006/0173313 A1 | 8/2006 | Liu et al. |
| 2006/0291707 A1 | 12/2006 | Kothapalli et al. |
| 2007/0057184 A1 | 3/2007 | Uto et al. |
| 2007/0133113 A1 | 6/2007 | Minabe et al. |
| 2007/0159639 A1 | 7/2007 | Teramura et al. |
| 2007/0171430 A1 | 7/2007 | Tearney et al. |
| 2007/0189436 A1 | 8/2007 | Goto et al. |
| 2008/0101664 A1 | 5/2008 | Perez |
| 2009/0046164 A1 | 2/2009 | Shroff et al. |
| 2009/0079987 A1 | 3/2009 | Ben-Ezra et al. |
| 2009/0125242 A1 | 5/2009 | Choi et al. |
| 2009/0284831 A1 | 11/2009 | Schuster et al. |
| 2009/0316141 A1 | 12/2009 | Feldkhun |
| 2010/0135547 A1 | 6/2010 | Lee et al. |
| 2010/0271705 A1 | 10/2010 | Hung |
| 2011/0075928 A1 | 3/2011 | Jeong et al. |
| 2011/0192976 A1 | 8/2011 | Own et al. |
| 2011/0235863 A1 | 9/2011 | Maiden |
| 2012/0069344 A1 | 3/2012 | Liu |
| 2012/0099803 A1 | 4/2012 | Ozcan et al. |
| 2012/0105618 A1 | 5/2012 | Brueck et al. |
| 2012/0118967 A1 | 5/2012 | Gerst |
| 2012/0157160 A1 | 6/2012 | Ozcan et al. |
| 2012/0218379 A1 | 8/2012 | Ozcan et al. |
| 2012/0248292 A1 | 10/2012 | Ozcan et al. |
| 2012/0250032 A1 | 10/2012 | Wilde et al. |
| 2012/0281929 A1 | 11/2012 | Brand et al. |
| 2013/0083886 A1 | 4/2013 | Carmi et al. |
| 2013/0093871 A1 | 4/2013 | Nowatzyk et al. |
| 2013/0094077 A1 | 4/2013 | Brueck et al. |
| 2013/0100525 A1 | 4/2013 | Chiang et al. |
| 2013/0170767 A1 | 7/2013 | Choudhury et al. |
| 2013/0182096 A1 | 7/2013 | Boccara et al. |
| 2013/0223685 A1 | 8/2013 | Maiden |
| 2014/0007307 A1 | 1/2014 | Routh, Jr. et al. |
| 2014/0029824 A1 | 1/2014 | Shi et al. |
| 2014/0043616 A1 | 2/2014 | Maiden et al. |
| 2014/0050382 A1 | 2/2014 | Adie et al. |
| 2014/0118529 A1 | 5/2014 | Zheng et al. |
| 2014/0126691 A1 | 5/2014 | Zheng et al. |
| 2014/0152801 A1 | 6/2014 | Fine et al. |
| 2014/0153692 A1 | 6/2014 | Larkin et al. |
| 2014/0160236 A1 | 6/2014 | Ozcan et al. |
| 2014/0267674 A1 | 9/2014 | Mertz et al. |
| 2014/0347672 A1 | 11/2014 | Pavillon et al. |
| 2014/0368812 A1 | 12/2014 | Humphry et al. |
| 2015/0036038 A1 | 2/2015 | Horstmeyer et al. |
| 2015/0054979 A1 | 2/2015 | Ou et al. |
| 2015/0160450 A1 | 6/2015 | Ou et al. |
| 2015/0264250 A1 | 9/2015 | Ou et al. |
| 2015/0331228 A1 | 11/2015 | Horstmeyer et al. |
| 2016/0088205 A1 | 3/2016 | Horstmeyer et al. |
| 2016/0178883 A1 | 6/2016 | Horstmeyer et al. |
| 2016/0202460 A1 | 7/2016 | Zheng |
| 2016/0210763 A1 | 7/2016 | Horstmeyer et al. |
| 2016/0216208 A1 | 7/2016 | Kim et al. |
| 2016/0216503 A1 | 7/2016 | Kim et al. |
| 2016/0266366 A1 | 9/2016 | Chung et al. |
| 2016/0320595 A1 | 11/2016 | Horstmeyer et al. |
| 2016/0320605 A1 | 11/2016 | Ou et al. |
| 2016/0341945 A1 | 11/2016 | Ou et al. |
| 2017/0299854 A1 | 10/2017 | Kim et al. |
| 2017/0354329 A1 | 12/2017 | Chung et al. |

FOREIGN PATENT DOCUMENTS

| | | |
|---|---|---|
| CN | 101872033 A | 10/2010 |
| CN | 102608597 A | 7/2012 |
| CN | 103201648 A | 7/2013 |
| JP | 2007-299604 A | 11/2007 |
| JP | 2010-012222 A | 1/2010 |
| KR | 10-1998-0075050 A | 11/1998 |
| WO | WO 99/53469 A1 | 10/1999 |
| WO | WO 2002/102128 A1 | 12/2002 |
| WO | WO 2003/062744 A1 | 7/2003 |
| WO | WO 2008/116070 A1 | 9/2008 |
| WO | WO 2011/093043 A1 | 8/2011 |
| WO | WO 2012/037182 A1 | 3/2012 |
| WO | WO 2014/070656 A1 | 5/2014 |
| WO | WO 2015/017730 A1 | 2/2015 |
| WO | WO 2015/027188 A1 | 2/2015 |
| WO | WO 2016/090331 | 6/2016 |
| WO | WO 2016/106379 A1 | 6/2016 |
| WO | WO 2016/118761 A1 | 7/2016 |
| WO | WO 2016/123156 A1 | 8/2016 |
| WO | WO 2016/123157 A1 | 8/2016 |
| WO | WO 2016/149120 A1 | 9/2016 |
| WO | WO 2016/187591 A1 | 11/2016 |
| WO | WO 2017081539 A1 | 5/2017 |
| WO | WO 2017081540 A1 | 5/2017 |
| WO | WO 2017081542 A2 | 5/2017 |

OTHER PUBLICATIONS

U.S. Appl. No. 15/160,941, filed May 20, 2016 entitled "Laser-Based Fourier Ptychographic Imaging Systems and Methods".
U.S. Office Action dated Oct. 5, 2015 in U.S. Appl. No. 14/065,305.
U.S. Notice of Allowance dated Dec. 4, 2015 in U.S. Appl. No. 14/065,305.
U.S. Notice of Allowance dated Jan. 14, 2016 in U.S. Appl. No. 14/448,850.
U.S. Notice of Allowance dated Jan. 22, 2016 in U.S. Appl. No. 14/466,481.
U.S. Notice of Allowance dated Apr. 13, 2016 in U.S. Appl. No. 14/448,850.
U.S. Notice of Allowance dated Apr. 22, 2016 in U.S. Appl. No. 14/466,481.
U.S. Office Action dated Jul. 14, 2016 in U.S. Appl. No. 15/007,196.
U.S. Notice of Allowance dated Aug. 23, 2016 in U.S. Appl. No. 14/466,481.
U.S. Office Action dated Aug. 16, 2016 in U.S. Appl. No. 14/065,280.
International Search Report and Written Opinion dated Feb. 21, 2014 in PCT/US2013/067068.
International Preliminary Report on Patentability dated May 14, 2015 in PCT/US2013/067068.
European Third-Party Observations, dated Jan. 20, 2016 in EP Application No. 13851670.3.
European Extended Search Report dated Mar. 31, 2016 in EP Application No. 13851670.3.

(56) References Cited

OTHER PUBLICATIONS

International Preliminary Report on Patentability dated Mar. 3, 2016 issued in PCT/US2014/052351.
International Search Report and Written Opinion dated Dec. 5, 2014 issued in PCT/US2014/052351.
International Search Report and Written Opinion dated Nov. 13, 2014 issued in PCT/US2014/049297.
International Preliminary Report on Patentability dated Feb. 11, 2016 issued in PCT/US2014/049297.
International Search Report and Written Opinion dated Feb. 22, 2016 issued in PCT/US2015/064126.
International Search Report and Written Opinion dated Apr. 19, 2016 issued in PCT/US2015/067498.
International Search Report and Written Opinion dated May 4, 2016 issued in PCT/US2016/015001.
International Search Report and Written Opinion dated May 11, 2016 issued in PCT/US2016/015002.
International Search Report and Written Opinion dated Jun. 27, 2016 issued in PCT/US2016/022116.
International Search Report and Written Opinion dated Jun. 30, 2016 issued in PCT/US2016/014343.
"About Molemap," Retrieved Oct. 23, 2015, 2 pages. [http://molemap.net.au/about-us/].
Abramomwitz, M. et al, "Immersion Media," Olympus Microscopy Resource Center, 2012, 6 pp. [http://www.olympusmicro.com/primer/anatomy/immersion.html].
Abramomwitz, M., et al, "Field Curvature," Olympus Microscopy Resource Center, 2012, 3 pp. [http://www.olympusmicro.com/primer/anatomy/fieldcurvature.html].
"Age-Related Macular Degeneration (AMD) | National Eye Institute." [Online]. Available: https://www.nei.nih.gov/eyedata/amd#top. [Accessed: Apr. 5, 2016].
Alexandrov, S., et al, "Spatial information transmission beyond a system's diffraction limit using optical spectral encoding of the spatial frequency," Journal of Optics A: Pure and Applied Optics 10, 025304 (2008).
Alexandrov, S.A., et al, "Synthetic Aperture Fourier holographic optical microscopy," Phys. Rev. Lett. 97, 168102 (2006).
Arimoto, H., et al, "Integral three-dimensional imaging with digital reconstruction," Opt. Lett. 26, 157-159 (2001).
Balan, R., et al, "On signal reconstruction without phase, Applied and Computational Harmonic Analysis 20," No. 3 (2006): 345-356.
Balan, R., et al, "Painless reconstruction from magnitudes of frame coefficients," J Fourier Anal Appl 15:488-501 (2009).
Bauschke, H.H., et al, "Phase retrieval, error reduction algorithm, and Fienup variants: a view from convex optimization," J Opt Soc Am A 19:1334-1345 (2002).
Becker, S., et al, "Templates for convex cone problems with applications to sparse signal recovery," Technical report, Department of Statistics, Stanford University, (2010), 48 Pages.
Betti, R., et al, "Observational study on the mitotic rate and other prognostic factors in cutaneous primary melanoma arising from naevi and from melanoma de novo," Journal of the European Academy of Dermatology and Venereology, 2014.
Bian, L., et al, "Fourier ptychographic reconstruction using Wirtinger flow optimization," Opt. Express 23:4856-4866 (2015).
Bian, Z., et al, "Adaptive system correction for robust Fourier ptychographic imaging," Optics express, 2013. 21(26): p. 32400-32410.
BioTek® Brochure: BioTek's Multi-Mode Microplate Reading Techonologies, 2016, 2 pp. [http://www.biotek.com].
Bishara, W., et al, "Holographic pixel super-resolution in portable lensless on-chip microscopy using a fiber-optic array," Lab Chip 11(7), 1276-1279 (2011).
Bishara, W., et al, "Lensfree on-chip microscopy over a wide field-of-view using pixel super-resolution," Opt. Express 18(11), 11181-11191 (2010).
Blum, A., et al, "Clear differences in hand-held dermoscopes," JDDG: Journal der Deutschen Dermatologischen Gesellschaft, 2006, 4(12): p. 1054-1057.
Blum, A., et al, Dermatoskopie von Hauttumoren: Auflichtmikroskopie; Dermoskopie; digitale Bildanalyse; mit 28 Tabellen. 2003: Springer DE, Chapter 4 "Dermatoskopisch sichtbare Strukturen" p. 15-66.
Born, M., et al, "Principles of Optics: Electromagnetic theory of propagation, interference and diffraction of light" 7th Ed., Cambridge Univ. Press, (1999) pp. 1-31.
Brady, D., et al, "Multiscale gigapixel photography," Nature 486, 386-389 (2012).
Burer, S., et al, "A nonlinear programming algorithm for solving semidefinite programs via low-rank factorization," Math Program, Ser B 95:329-357 (2003).
Burer, S., et al, "Local minima and convergence in low-rank semidefinite programming. Math Program," Ser A 103:427-444 (2005).
Candes, E.J., et al, "Phase retrieval via matrix completion," SIAM J. Imaging Sci. 6:199-225 (2012).
Candes, E.J., et al, "Phase retrieval via Wirtinger flow: theory and algorithms," IEEE Trans. Info. Theory 61:1985-2007 (2015).
Candes, E.J., et al, "PhaseLift: exact and stable signal recovery from magnitude measurements via convex programming.," Comm Pure Appl Math 66:1241-1274 (2013).
Carroll, J., "Adaptive optics retinal imaging: applications for studying retinal degeneration," Arch. Ophthalmol., vol. 126, pp. 857-858, 2008.
Chao, W. et al, "Soft X-ray microscopy at a spatial resolution better than 15 nm," Nature Letters, vol. 435/30, (Jun. 2005) pp. 1210-1213.
Chen, T., et al, "Polarization and phase shifting for 3D scanning of translucent objects," Proc. CVPR, (2007).
Chin, L., et al, "Malignant melanoma: genetics and therapeutics in the genomic era," Genes & development, 2006, 20(16): p. 2149-2182.
Choi, W., et al, "Tomographic phase microscopy," Nature Methods 4(9) (2007), pp. 1-3 Published Online Aug. 12, 2007.
Chung, J., et al, "Counting White Blood Cells from a Blood Smear Using Fourier Ptychographic Microscopy," PLoS One 10(7), e0133489 (2015).
Chung, J., et al, "Wide field-of-view fluorescence image deconvolution with aberration-estimation from Fourier ptychography," Feb. 1, 2016, vol. 7, No. 2, Biomedical Optics Express 352.
Colomb, T., et al, "Automatic procedure for aberration compensation in digital holographic microscopy and applications to specimen shape compensation," Appl. Opt. 45, 851-863 (2006).
De Sa, C., et al, "Global convergence of stochastic gradient descent for some non convex matrix problems," Proc. 32nd Int. Conf. Machine Learning (2015), 10 pp.
Debailleul, M., et al, "High-resolution three-dimensional tomographic diffractive microscopy of transparent inorganic and biological samples," Optic Letters 34 (2008).
Denis, L., et al, "Inline hologram reconstruction with sparsity constraints," Opt. Lett. 34, pp. 3475-3477 (2009).
Di, J., et al, "High resolution digital holographic microscopy with a wide field of view based on a synthetic aperture technique and use of linear CCD scanning," Appl. Opt. 47, pp. 5654-5659 (2008).
Dierolf, M., et al, "Ptychographic coherent diffractive imaging of weakly scattering specimens," New J. Phys. 12, 035017 (2010).
Dierolf, M., et al, "Ptychographic X-ray computed tomography at the nanoscale," Nature, vol. 467, pp. 436-439, (2010).
"Doctor Mole—Skin Cancer App," Retrieved Oct. 23, 2015, 1 page. [http://www.doctormole.com].
Dong, S., et al, "FPscope: a field-portable high-resolution microscope using a cellphone lens," Biomed. Opt. Express 5(10), 3305-3310 (2014).
Dong, S., et al, "High-resolution fluorescence imaging via pattern-illuminated Fourier ptychography," Opt. Express 22(17), 20856-20870 (2014).
Dong, S., et al, "Aperture-scanning Fourier ptychography for 3D refocusing and super-resolution macroscopic imaging," pp. 13586-13599 (Jun. 2, 2014).
Eldar, Y.C., et al, "Sparse phase retrieval from short-time Fourier measurements," IEEE Signal Processing Letters 22, No. 5 (2015): 638-642.

(56) References Cited

OTHER PUBLICATIONS

Emile, O., et al, "Rotating polarization imaging in turbid media," Optics Letters 21(20), (1996).
Faulkner, H.M.L., and Rodenburg, J.M., "Error tolerance of an iterative phase retrieval algorithm for moveable illumination microscopy," Ultramicroscopy 103(2), 153-164 (2005).
Faulkner, H.M.L., and Rodenburg, J.M., "Movable aperture lensless transmission microscopy: a novel phase retrieval algorithm," Phys. Rev. Lett. 93, 023903 (2004).
Fazel, M., "Matrix rank minimization with applications," PhD Thesis (Stanford University, Palo Alto, CA). (2002).
Feng, P., et al, "Long-working-distance synthetic aperture Fresnel off-axis digital holography," Optics Express 17, pp. 5473-5480 (2009).
Fienup, J. R., "Invariant error metrics for image reconstruction," Appl. Opt. 36(32), 8352-8357 (1997).
Fienup, J. R., "Lensless coherent imaging by phase retrieval with an illumination pattern constraint," Opt. Express 14, 498-508 (2006).
Fienup, J. R., "Phase retrieval algorithms: a comparison," Appl. Opt. 21, 2758-2769 (1982).
Fienup, J. R., "Reconstruction of a complex-valued object from the modulus of its Fourier transform using a support constraint," J. Opt. Soc. Am. A 4, 118-123 (1987).
Fienup, J. R., "Reconstruction of an object from the modulus of its Fourier transform," Opt. Lett. 3, 27-29 (1978).
Gan, X., et al, "Image enhancement through turbid media under a microscope by use of polarization gating methods," JOSA A 16(9), (1999).
Gerke T.D., et al, "Aperiodic volume optics," Nature Photonics (2010), vol. 4, pp. 188-193.
Ghosh, A., et al, "Multiview face capture using polarized spherical gradient illumination," ACM Transactions on Graphics 30(6) (2011).
Godara, P., et al, "Adaptive optics retinal imaging: emerging clinical applications.," Optom. Vis. Sci., vol. 87, No. 12, pp. 930-941, Dec. 2010.
Goodman, J.W., "Introduction to Fourier Optics," Roberts & Company Publication, Third Edition, chapters 1-6, pp. 1-172 (2005).
Goodson, A.G., et al, "Comparative analysis of total body and dermatoscopic photographic monitoring of nevi in similar patient populations at risk for cutaneous melanoma," Dermatologic Surgery, 2010. 36(7): p. 1087-1098.
Granero, L., et al, "Synthetic aperture superresolved microscopy in digital lensless Fourier holography by time and angular multiplexing of the object information," Appl. Opt. 49, pp. 845-857 (2010).
Grant, M., et al, "CVX: Matlab software for disciplined convex programming," version 2.0 beta. http://cvxr.com/cvx, (Sep. 2013), 3 pages.
Greenbaum, A., et al, "Field-portable wide-field microscopy of dense samples using multi-height pixel super resolution based lensfree imaging," Lab Chip 12(7), 1242-1245 (2012).
Greenbaum, A., et al, "Increased space—bandwidth product in pixel super-resolved lensfree on-chip microscopy," Sci. Rep. 3, p. 1717 (2013).
Gruev, V., et al, "Dual-tier thin film polymer polarization imaging sensor," Optics Express, vol. 18, No. 18, 12 pages (2010).
Guizar-Sicairos, M., and Fienup, J.R.,"Phase retrieval with transverse translation diversity: a nonlinear optimization approach," Opt. Express 16, 7264-7278 (2008).
Gunturk, B.K., et al, "Image Restoration: Fundamentals and Advances," vol. 7, Chapter 3, pp. 63-68 (CRC Press, 2012).
Gustafsson, M.G.L., "Surpassing the lateral resolution limit by a factor of two using structured illumination microscopy," J. Microsc. 198, 82-87 (2000).
Gutzler, T., et al, "Coherent aperture-synthesis, wide-field, high-resolution holographic microscopy of biological tissue," Opt. Lett. 35, pp. 1136-1138 (2010).
Haigh, S. J., et al, (2009) "Atomic structure imaging beyond conventional resolution limits in the transmission electron microscope"; Physical Review Letters 103. 126101-1 126101-4.

Han, C., et al, "Wide Field-of-View On-Chip Talbot Fluorescence Microscopy for Longitudinal Cell Culture Monitoring from within the Incubator" Anal. Chem. 85(4), 2356-2360 (2013).
Hillman, T.R., et al, "High-resolution, wide-field object reconstruction with synthetic aperture Fourier holographic optical microscopy," Opt. Express 17, pp. 7873-7892 (2009).
Hofer, H., et al, "Dynamics of the eye's wave aberration," J. Opt. Soc. Am. A, vol. 18, No. 3, p. 497, 2001.
Hofer, H., et al, "Organization of the human trichromatic cone mosaic.," J. Neurosci., vol. 25, No. 42, pp. 9669-9679, Oct. 2005.
Hong, S-H., et al, "Three-dimensional volumetric object reconstruction using computational integral imaging," Opt. Express 12, 483-491 (2004).
Hoppe, W., "Diffraction in inhomogeneous primary wave fields. 1. Principle of phase determination from electron diffraction interference," Acta Crystallogr. A25, 495-501 1969.
Horstmeyer, R., et al, "A phase space model of Fourier ptychographic microscopy," Optics Express, 2014. 22(1): p. 338-358.
Horstmeyer, R., et al, "Digital pathology with fourier ptychography," Comput. Med. Imaging Graphics 42, 38-43 (2015).
Horstmeyer, R., et al, "Overlapped fourier coding for optical aberration removal," Manuscript in preparation, 19 pages (2014).
Horstmeyer, R., et al, "Solving ptychography with a convex relaxation," Physics Optics (2014) 1-8 pages.
Hüe, F., et al, "Wave-front phase retrieval in transmission electron microscopy via ptychography," Phys. Rev. B 82, 121415 (2010).
Humphry, M., et al, "Ptychographic electron microscopy using high-angle dark-field scattering for sub-nanometre resolution imaging," Nat. Commun. 3, 730 (2012).
IncuCyte® ZOOM System, Brochure, 1-4 pp. (2016) (retrieved Feb. 25, 2016), [http://www.essenbioscience.com/media/uploads/files/8000-0333-E00-IncuCyte_ZOOM_brochure.pdf].
Jaganathan, K., et al, "Recovery of sparse 1-D signals from the magnitudes of their Fourier transform," IEEE International Symposium on Information Theory Proceedings (2012): 1473-1477.
Jaganathan, K., et al, "Phase retrieval with masks using convex optimization," IEEE International Symposium on Information Theory Proceedings (2015): 1655-1659.
Jaganathan, K., et al, "STFT Phase retrieval: uniqueness guarantees and recovery algorithms," arXiv preprint arXiv:1508.02820 (2015).
Joeres, S., et al, "Retinal imaging with adaptive optics scanning laser ophthalmoscopy in unexplained central ring scotoma.," Arch. Ophthalmol., vol. 126, No. 4, pp. 543-547, Apr. 2008.
Jung, J.H., et al, "Microfluidic-integrated laser-controlled microactuators with on-chip microscopy imaging functionality," Lab Chip 14 (19), Oct. 7, 2014, pp. 3781-3789.
Kay, D. B., et al, "Outer retinal structure in best vitelliform macular dystrophy.," JAMA Ophthalmol., vol. 131, pp. 1207-1215, 2013.
Kim, J., et al, Incubator embedded cell culture imaging system (EmSight) based on Fourier ptychographic microscopy. EmSight manuscript, Optical Society of America, 2015.
Kim, M., et al, "High-speed synthetic aperture microscopy for live cell imaging," Opt. Lett. 36, pp. 148-150 (2011).
Kirkland, A.I., et al, "Multiple beam tilt microscopy for super resolved imaging;" Japanese Society of Electron Microscopy: Journal of Electron Microscopy I: 11-22(1997), vol. 46, No. 1 1997.
Kirkland, A.I., et al, "Super-resolution by aperture synthesis: tilt series reconstruction in CTEM," Ultramicroscopy 57, (1995) 355-374, Received May 27, 1994, in final form Oct. 2, 1994; 1995 Elsevier Science B.V. SSDI 0304-3991(94)00191-x.
Kittler, H., et al, "Morphologic changes of pigmented skin lesions: a useful extension of the ABCD rule for dermatoscopy," Journal of the American Academy of Dermatology, 1999. 40(4): p. 558-562.
Kozak, I., "Retinal imaging using adaptive optics technology.," Saudi J. Ophthalmol. Off. J. Saudi Ophthalmol. Soc., vol. 28, No. 2, pp. 117-122, Apr. 2014.
Lauer, V., "New Approach to optical diffraction tomography yielding a vector equation of diffraction tomography and a novel tomography microscope," Journal of Microscopy, vol. 205, Pt 2 Feb. 2002, pp. 165-176, The Royal Microscopical Society 2001.
Lee, K., et al, "Synthetic Fourier transform light scattering," Optics Express 21 (2013).

(56) References Cited

OTHER PUBLICATIONS

Levoy, M., et al, "Light field microscopy," ACM Trans. Graphics 25, (2006).

Levoy, M., et al., "Recording and controlling the 4D light field in a microscope using microlens arrays," J. Microsc. 235 (2009).

Li, X., et al., "Sparse signal recovery from quadratic measurements via convex programming," SIAM Journal on Mathematical Analysis 45, No. 5 (2013): 3019-3033.

Lohmann, A. W., et al, "Space—bandwidth product of optical signals and systems," J. Opt. Soc. Am. A 13, pp. 470-473 (1996).

Lue, N., et al, "Live Cell Refractometry Using Hilbert Phase Microscopy and Confocal Reflectance Microscopy," The Journal of Physical Chemistry A, 113, pp. 13327-13330 (2009).

Luxexcel® Brochure, Luxexcel: 3D Printing Service Description, Retrieved Mar. 7, 2016, 5 pp. [http://www.luxexcel.com].

"Lytro," Retrieved Oct. 23, 2015, 6 pp. [https://www.lytro.com/].

Ma, W., et al, "Rapid Acquisition of Specular and Diffuse Normal Maps from Polarized Spherical Gradient Illumination," University of Southern California, Institute for Creative Technologies, 12 pages (2007).

Mahajan, V. N., "Zernike circle polynomials and optical aberrations of systems with circular pupils," Appl. Opt. 33(34), 8121-8124 (1994).

Maiden, A. M., et al, "A new method of high resolution, quantitative phase scanning microscopy," in: M.T. Postek, D.E. Newbury, S.F. Platek, D.C. Joy (Eds.), SPIE Proceedings of Scanning Microscopy, 7729, 2010.

Maiden, A. M., et al, "An improved ptychographical phase retrieval algorithm for diffractive imaging," Ultramicroscopy 109(10), 1256-1262 (2009).

Maiden, A. M., et al, "Superresolution imaging via ptychography," Journal of the Optical Society of America A. Apr. 2011, vol. 28 No. 4, pp. 604-612.

Maiden, A. M., et al, "Optical ptychography: a practical implementation with useful resolution," Opt. Lett. 35, 2585-2587 (2010).

Marchesini S., "A unified evaluation of iterative projection algorithms for phase retrieval," Rev Sci Instrum 78:011301 (2007).

Marchesini S., et al, "Augmented projections for ptychographic imaging," Inverse Probl 29:115009 (2013).

Marrison, J., et al, "Ptychography—a label free, high-contrast imaging technique for live cells using quantitative phase information," Sci. Rep. 3, 2369 (2013).

Medoff, B.P., et al, "Iterative convolution backprojection algorithms for image reconstruction from limited data," J. Opt. Soc. Am. vol. 73, No. 11, Nov. 1983, pp. 1493-1500.

"Melafind," Retrieved Oct. 23, 2015, 4 pages. [http://www.melafind.com/].

Meyer, R.R., et al, "A method for the determination of the wave aberration function of high-resolution TEM," Ultramicroscopy 99 (2004) 115-123: Elsevier B.V. Doi: 10.1016/j.ultramic.2003.11.001.

Miao, J., et al, "High Resolution 3D X-Ray Diffraction Microscopy," Physical Review Letters, Aug. 19, 2002, vol. 89, No. 8, pp. 1-4.

Mico, V., et al, "Synthetic aperture microscopy using off-axis illumination and polarization coding," Optics Communications, pp. 276, 209-217 (2007).

Mico, V., et al, "Synthetic aperture superresolution with multiple off-axis holograms," JOSA A 23, pp. 3162-3170 (2006).

Mir, M. et al, "Optical measurement of cycle-dependent cell growth," Proceedings of the National Academy of Sciences 108, pp. 13124-13129 (2011).

Mir, M., et al, "Blood screening using diffraction phase cytometry," Journal of Biomedical Optics 15, pp. 027016-027014 (2010).

Moreno, I., "Creating a desired lighting pattern with an LED array," 8th International Conference on Solid State Lighting, Proceedings of SPIE, vol. 7058, 2008, 9 pp.

Mrejen, S., et al, "Adaptive optics imaging of cone mosaic abnormalities in acute macular neuroretinopathy.," Ophthalmic Surg. Lasers Imaging Retina, vol. 45, No. 6, pp. 562-569, Jan. 2014.

Nayar, S. K., et al, "Fast separation of direct and global components of a scene using high frequency illumination," ACM Transactions on Graphics 25(3) (2006).

Ng, R., et al, "Light field photography with a hand-held plenoptic camera", Computer Science Technical Report CSTR, 2005. 2(11).

Nomura, H., and Sato, T., "Techniques for measuring aberrations in lenses used in photolithography with printed patterns," Appl. Opt. 38(13), 2800-2807 (1999).

Ohlsson, H., et al, "Compressive phase retrieval from squared output measurements via semidefinite programming," arXiv:1111.6323 (2011).

Ou, X., et al, "High numerical aperture Fourier ptychography: principle, implementation and characterization," Opt. Express 23:3472-3491 (2015).

Ou, X., et al, "Quantitative phase imaging via Fourier ptychographic microscopy," Optics Letters, 2013. 38(22): p. 4845-4848.

Ou. X., et al, "Embedded pupil function recovery for Fourier ptychographic microscopy," Optics Express 22 (5), pp. 4960-4972 (2014), with Erratum (2015).

Ou. X., et al, "Embedded pupil function recovery for Fourier ptychographic microscopy," submitted Dec. 26, 2013; 13 pp.

Pacheco, S., et al, "Reflective Fourier Ptychography," J. Biomed. Opt. 21(2), pp. 026010-1-026010-7, (Feb. 18, 2016). [http://biomedicaloptics.spiedigitallibrary.org].

Recht, B., et al, "Guaranteed minimum-rank solutions of linear matrix equations via nuclear norm minimization," SIAM Review 52, No. 3 (2010): 471-501.

Reinhard, E., et al, "High Dynamic Range Imaging: Acquisition, Display, and Image-based Lighting" (Morgan Kaufmann, 2010).

Rodenburg, J. M., et al, "A phase retrieval algorithm for shifting illumination," Appl. Phys. Lett 85, 4795-4797 (2004).

Rodenburg, J. M., et al, "Hard-X-ray lensless imaging of extended objects," Phys. Rev. Lett. 98, 034801 (2007).

Rodenburg, J. M., et al, "The theory of super-resolution electron microscopy via Wigner-distribution deconvolution," Phil. Trans. R. Soc. Lond. A 339, 521-553 (1992).

Rodenburg, J., "Ptychography and related diffractive imaging methods," Adv. Imaging Electron Phys.150, 87-184 (2008).

Rossi, E.A., et al, "In vivo imaging of retinal pigment epithelium cells in age related macular degeneration.," Biomed. Opt. Express, vol. 4, No. 11, pp. 2527-2539, Jan. 2013.

Rowe, M., et al, "Polarization-difference imaging: a biologically inspired technique for observation through scattering media," Optics Letters, vol. 20, No. 6, 3 pages (1995).

Schechner, Y., "Multiplexing for Optimal Lighting," IEEE Transactions on Pattern Analysis and Machine Intelligence, vol. 29, No. 8, 1339-1354 (2007).

Schnars, U., et al, "Digital recording and numerical reconstruction of holograms," Measurement Science and Technology, 13, R85 (2002).

Schwarz, C., et al, "Imaging interferometric microscopy," Optics letters 28, pp. 1424-1426 (2003).

Shechner, Y., et al, "Polarization-based vision through haze," Applied Optics 42(3), (2003).

Shechtman, Y., et al, "Sparsity based sub-wavelength imaging with partially incoherent light via quadratic compressed sensing," Opt Express 19:14807-14822 (2011).

Siegel, R., et al, "Cancer statistics 2013," CA: a cancer journal for clinicians, 2013. 63(1): p. 11-30.

Stoecker, W., et al, "Diagnostic Inaccuracy of Smartphone Applications for Melanoma Detection: Representative Lesion Sets and the Role for Adjunctive Technologies," JAMA Dermatology, 2013. 149(7): p. 884.

Sun, D., et al, "Estimating a signal from a magnitude spectrogram via convex optimization," arXiv:1209.2076 (2012).

Sun, J., et al, "Coded multi-angular illumination for Fourier ptychography based on Hadamard codes," 5 pages (2015).

Tam, K., et al, "Tomographical imaging with limited-angle input," J. Opt. Soc. Am. 21 (1981).

Thibault, P. et al, "Probe retrieval in ptychographic coherent diffractive imaging," Ultramicroscopy 109(4), 338-343 (2009).

(56) References Cited

OTHER PUBLICATIONS

Thibault, P., et al, "High-resolution scanning X-ray diffraction microscopy," Science 321, 2008, pp. 379-382.
Thomas, L., et al, "Semiological value of ABCDE criteria in the diagnosis of cutaneous pigmented tumors," Dermatology, 1998. 197(1): p. 11-17.
Tian, L., et al, "Multiplexed Coded Illumination for Fourier Ptychography with an LED Array Microscope," Optical Society of America, 14 pages (2014).
Tippie, A.E., et al, "High-resolution synthetic-aperture digital holography with digital phase and pupil correction," Opt. Express 19, pp. 12027-12038 (2011).
Turpin, T., et al, "Theory of the synthetic aperture microscope," pp. 230-240 (1995).
Tyson, R., "Principles of Adaptive Optics" (CRC Press, 2010).
Vulovic, M., et al, "When to use the projection assumption and the weak-phase object approximation in phase contrast cryo-EM," Ultramicroscopy 136 (2014) 61-66.
Waldspurger, I., et al, "Phase recovery, maxcut and complex semidefinite programming," Mathematical Programming 149, No. 1-2 (2015): 47-81.
Wang, Q., et al, "Adaptive Optics Microperimetry and OCT Images Show Preserved Function and Recovery of Cone Visibility in Macular Telangiectasia Type 2 Retinal Lesions," Invest. Ophthalmol. Vis. Sci., vol. 56, pp. 778-786 (2015).
Wang, Z., et al, "Tissue refractive index as marker of disease," Journal of Biomedical Optics 16, 116017-116017 (2011).
Watanabe, M., et al, "Telecentric optics for focus analysis," IEEE trans. pattern. anal. mach. intell., 19 1360-1365 (1997).
Wesner, J., et al, "Reconstructing the pupil function of microscope objectives from the intensity PSF," in Current Developments in Lens Design and Optical Engineering III, R. E. Fischer, W. J. Smith, and R. B. Johnson, eds., Proc. SPIE 4767, 32-43 (2002).
Williams, A., et al, "Fourier ptychographic microscopy for filtration-based circulating tumor cell enumeration and analysis," J. Biomed. Opt. 19(6), 066007 (2014).
Wolf, J., et al, "Diagnostic Inaccuracy of Smartphone Applications for Melanoma Detection," JAMA Dermatology, 2013, 149(7): p. 885-885.
Wu, J., et al, "Focal plane tuning in wide-field-of-view microscope with Talbot pattern illumination," Opt. Lett. 36, 2179-2181 (2011).
Wu, J., et al, "Wide field-of-view microscope based on holographic focus grid illumination," Opt. Lett. 35, 2188-2190 (2010).
Xu, W., et al, "Digital in-line holography for biological applications," Proc. Natl Acad. Sci. USA 98, pp. 11301-11305 (2001).
Yuan, C., et al, "Angular multiplexing in pulsed digital holography for aperture synthesis," Optics Letters 33, pp. 2356-2358 (2008).
Zeiss, C., "Microscopy, Cells Need the Perfect Climate, System Solutions for Live Cell Imaging under Physiological Conditions," printed Feb. 2008, 1-42 pgs.
Zhang, Y., et al, "Self-learning based fourier ptychographic microscopy," Optics Express, 16pgs (2015).
Zhang, Y., et al, "Photoreceptor Perturbation Around Subretinal Drusenoid Deposits as Revealed by Adaptive Optics Scanning Laser Ophthalmoscopy," Am. J. Ophthalmol., vol. 158, No. 3, pp. 584-596, 2014.
Zheng, G., et al, "Characterization of spatially varying aberrations for wide field-of-view microscopy," Opt. Express 21, 15131-15143 (2013).
Zheng, G., et al, "Microscopy refocusing and dark-field imaging by using a simple LED array," Opt. Lett. 36, 3987-3989 (2011).
Zheng, G., et al, "0.5 gigapixel microscopy using a flatbed scanner," Biomed. Opt. Express 5, 1-8 (2014).
Zheng, G., et al, "Sub-pixel resolving optofluidic microscope for on-chip cell imaging," Lab Chip 10, pp. 3125-3129 (2010).
Zheng, G. "The ePetri dish, an on-chip cell imaging platform based on subpixel perspective sweeping microscopy (SPSM)," Proc. Natl. Acad. Sci. USA 108, pp. 16889-16894 (2011).
Zheng, G., et al, "Wide-field, high-resolution Fourier ptychographic microscopy," Nature Photonics, vol. 7, pp. 739-745, Published Online Jul. 28, 2013 at www.nature.com/naturephotonics.
Chung, J., et al, "Wide-field Fourier ptychographic microscopy using laser illumination source," Optical Society of America, 13 pgs., Mar. 23, 2016.
Guo, K., et al, "Optimization of sampling pattern and the design of Fourier ptychographic illuminator," Optical Society of America; Optics Express, vol. 23, No. 5, pp. 6171-6180 (2015).
Phillips, Z., et al, "Multi-Contrast Imaging and Digital Refocusing on a Mobile Microscope with a Domed LED Array," PLoS One, 10 (5), pp. 1-13 (2015).
Horstmeyer, R., et al, "Standardizing the resolution claims for coherent microscopy," Nature Photonics, vol. 10, pp. 68-71, Feb. 2016.
Horstmeyer, R., et al, "Solving ptychography with a convex relaxation," New Journal of Physics, vol. 17 (2015) 1-14 pages.
Preliminary Amendment dated Mar. 17, 2014 filed in U.S. Appl. No. 14/065,280.
Preliminary Amendment dated Apr. 25, 2016 filed in U.S. Appl. No. 14/710,947.
Preliminary Amendment dated Nov. 28, 2016 filed in U.S. Appl. No. 15/206,859.
Preliminary Amendment dated Mar. 17, 2014 filed in U.S. Appl. No. 14/065,305.
Preliminary Amendment dated Nov. 28, 2016 filed in U.S. Appl. No. 15/209,604.
U.S. Office Action dated Sep. 16, 2016 I U.S. Appl. No. 14/065,305.
U.S. Notice of Allowance dated Nov. 2, 2016 in U.S. Appl. No. 14/572,493.
U.S. Office Action dated Nov. 22, 2016 in U.S. Appl. No. 15/003,559.
U.S. Supplemental Notice of Allowance dated Dec. 12, 2016 in U.S. Appl. No. 14/572,493.
U.S. Notice of Allowance dated Jan. 13, 2017 in U.S. Appl. No. 14/065,305.
U.S. Final Office Action dated Jan. 23, 2017 in U.S. Appl. No. 15/007,196.
U.S. Office Action dated Feb. 21, 2017 in U.S. Appl. No. 14/960,252.
U.S. Supplemental Notice of Allowability dated Mar. 2, 2017 in U.S. Appl. No. 14/065,305.
U.S. Notice of Allowance dated Mar. 8, 2017 in U.S. Appl. No. 14/572,493.
U.S. Office Action dated Mar. 13, 2017 in U.S. Appl. No. 14/658,019.
U.S. Notice of Allowance dated Mar. 22, 2017 in U.S. Appl. No. 15/007,196.
U.S. Office Action dated Mar. 24, 2017 in U.S. Appl. No. 14/710,947.
U.S. Notice of Allowance dated Mar. 31, 2017 in U.S. Appl. No. 14/572,493.
U.S. Final Office Action dated Apr. 3, 2017 in U.S. Appl. No. 14/065,280.
U.S. Notice of Allowance dated Jun. 9, 2017 in U.S. Appl. No. 14/065,305.
U.S. Notice of Allowance dated Jun. 9, 2017 in U.S. Appl. No. 15/206,859.
U.S. Notice of Allowance dated Jun. 9, 2017 in U.S. Appl. No. 15/007,196.
U.S. Notice of Allowance dated Jun. 20, 2017 in U.S. Appl. No. 14/572,493.
U.S. Supplemental Notice of Allowance dated Jun. 28, 2017 in U.S. Appl. No. 15/206,859.
U.S. Final Office Action dated Jul. 27, 2017 in U.S. Appl. No. 15/003,559.
U.S. Notice of Allowance dated Aug. 16, 2017 in U.S. Appl. No. 15/209,604.
International Search Report and Wrtitten Opinion dated Sep. 5, 2016 issued in PCT/US2016/033638.
Chinese Office Action [Description in English] dated Jul. 11, 2016 issued in Application No. CN 201380068831.6.

(56) References Cited

OTHER PUBLICATIONS

Chinese Office Action [Description in English] dated Dec. 13, 2016 issued in Application No. CN201480057911.6.
Extended European Search Report dated Feb. 16, 2017 issued in Application No. 14837844.1.
Extended European Search Report dated Feb. 15, 2017 issued in Applicatoin No. 14832857.8.
Chinese Second Office Action [Description in English] dated Feb. 17, 2017 issued in Application No. CN201380068831.6.
International Preliminary Report on Patentability dated Jun. 15, 2017 issued in Application No. PCT/US2015/064126.
European Office Action dated May 16, 2017 issued in European Patent Application No. 13851670.3.
International Preliminary Report on Patentability dated Jul. 6, 2017 issued in Application No. PCT/US2015/067498.
International Preliminary Report on Patentability dated Aug. 3, 2017 issued in Application No. PCT/US2016/014343.
International Preliminary Report on Patentability dated Aug. 10, 2017 issued in Application No. PCT/US2016/015001.
International Preliminary Report on Patentability dated Aug. 10, 2017 issued in Application No. PCT/US2016/015002.
Bian, L., et al, "Fourier ptychographic reconstruction using Poisson maximum likelihood and truncated Wirtinger gradient," Nature Publishing Group; Scientific Reports, vol. 6, No. 27384, Jun. 10, 2016, pp. 1-10. <doi: 10.1038/srep27384>.
Bunk, O., et al, "Influence of the overlap parameter on the convergence of the ptychographical iterative engine," Ultramicroscopy, vol. 108, (2008), pp. 481-487. <doi: 10.1016/j.ultramic.2007.08.003>.
Chai, A., et al, "Array imaging using intensity-only measurements," IOP Publishing: Inverse Problems, vol. 27, No. 1, Jan. 2011, pp. 1-16. <doi:10.1088/0266-5611/27/1/015005>.
Hoppe, W., "Diffraction in inhomogeneous primary wave fields. 1. Principle of phase determination from electron diffraction interference." Acta Crystallographica Section a—Crystal Physics Diffraction Theoretical and General Crystallography, A25, Jan. 1, 1969, pp. 495-501. (English Machine Translation Incl.).
Horstmeyer, R., et al, "Diffraction tomography with Fourier ptychography," Optica, Optical Society of America, vol. 3, No. 8, Aug. 2016, pp. 827-835. <doi:10.1364/OPTICA.3.000827>.
Lu, H., et al, "Quantitative phase imaging and complex field reconstruction by pupil modulation differential phase contrast," Optics Express, vol. 24, No. 22, Oct. 31, 2016, pp. 25345-25361. <doi:10.1364/OE.24.025345>.
Ou, X., et al, "Aperture scanning Fourier ptychographic microscopy," Biomedical Optics Express, vol. 7, No. 8, Aug. 1, 2016, pp. 3140-3150. <doi:10.1364/BOE.7.003140>.
Reinhard, E., et al, "High Dynamic Range Imaging: Acquisition, Display, and Image-based Lighting" Second Edition § 5.2 HDR Image Capture: Morgan Kaufmann, May 28, 2010, pp. 148-151. <ISBN: 9780123749147>.
Tian, L., et al, "3D differential phase-contrast microscopy with computational illumination using an LED array," Optics Letters, vol. 39, No. 5, Mar. 1, 2014, pp. 1326-1329. <doi:10.1364/OL39.001326>.
Tian, L., et al, "Computional illumination for high-speed in vitro Fourier ptychographic microscropy," Optica: Research Article, vol. 2, No. 10, Oct. 14, 2015, pp. 904-911. <doi:10.1364/OPTICA.2.000904>.
Wu, J., et al, "Harmonically matched grating-based full-field quantitative high-resolution phase microscope for observing dynamics of transparent biological samples," Optics Express, vol. 15, No. 26, Dec. 24, 2007, pp. 18141-18155. <doi:10.1364/OE.15.018141>.
Wu, J., et al, "Paired-angle-rotation scanning optical coherence tomography forward-imaging probe," Optics Letters, vol. 31, No. 9, May 1, 2006, pp. 1265-1267. <doi:10.1364/OL.31.001265>.
Yeh, et al., "Experimental robustness of Fourier ptychography phase retrieval algorithms," Optics Express, vol. 23, No. 26, Dec. 28, 2015, pp. 33214-33240. <doi: 10.1364/OE.23.033214>.
Zheng, G., "Fourier Ptychographic Imaging: A MATLAB tutorial," IOP Concise Physics, Morgan & Claypool Publication, San Rafael, CA., May 2016, pp. 96. <ISBN: 978-1-6817-4272-4 (ebook)> <doi: 10.1088/978-1-6817-4273-1>.
U.S. Appl. No. 15/620,674, filed Jun. 12, 2017, Chung, J. et al.
U.S. Appl. No. 15/636,494, filed Jun. 28, 2017, Kim, J. et al.
Office Action dated Aug. 31, 2017 in U.S. Appl. No. 15/636,494.
U.S. Notice of Allowance dated Sep. 1, 2017 in U.S. Appl. No. 15/206,859.
Notice of Allowance dated Sep. 20, 2017 in U.S. Appl. No. 15/007,196.
Notice of Allowance dated Oct. 11, 2017 in U.S. Appl. No. 14/572,493.
Office Action dated Nov. 3, 2017 in U.S. Appl. No. 15/068,389.
Office Action dated Nov. 30, 2017 in U.S. Appl. No. 15/007,159.
Chinese Office Action [Description in English] dated May 31, 2016 issued in Application No. CN 201380068831.6.
Chinese Second Office Action [Description in English] dated Jan. 22, 2017 issued in Application No. CN201380068831.6.
Chinese Third Office Action [Summary in English] dated Jul. 24, 2017 issued in Application No. 201380068831.6.
Chinese First Office Action [Summary in English] dated Aug. 2, 2017 issued in Application No. CN 201480054301.0.
Australian Office Action dated Sep. 18, 2017 issued in Application No. AU 2014296034.
International Preliminary Report on Patentability dated Sep. 28, 2017 issued in Application No. PCT/US2016/022116.
Japanese Office Action dated Oct. 17, 2017 issued in Application No. 2015-539884.
Chinese Office Action [Summary in English] dated Oct. 26, 2017 issued in CN 201480057911.6.
International Preliminary Report on Patentability dated Nov. 30, 2017 issued in PCT/US2016/033638.
Abrahamsson, S., et al., "Fast multicolor 3D imaging using aberration-corrected mulitfocus microscopy," Brief Communications: Nature Methods, vol. 10, No. 1, Jan. 2013, pp. 60-65. <doi:10.1038/nmeth.2277>.
Holloway, J., et al. "SAVI: Synthetic apertures for long-range, subdiffraction-limited visible imaging using Fourier ptychography," Science Advances| Research Article, vol. 3, No. 4, Apr. 14, 2017, pp. 1-11. <doi:10.1126/sciadv.1602564> [retrieved on Nov. 28, 2017] <URL:http://advances.sciencemag.org/>.
Kawata, S. et al, "Optical microscope tomography. I. Support constraint," Journal Optical Society America A, vol. 4, No. 1, Jan. 1987, pp. 292-297. <doi:10.1364/JOSAA.4.000292>.
Kim, M., et al, "High-speed synthetic aperture microscopy for live cell imaging," Optics Letters, vol. 36, No. 2, Jan. 15, 2011, pp. 148-150. <doi:10.1364/OL.36.000148>.
Kner, P., "Phase diversity for three-dimensional imaging," Journal of the Optical Society of America A, vol. 30, No. 10, Oct. 1, 2013, pp. 1980-1987. <doi:10.1364/JOSAA.30.001980>.
Sankaranarayanan, Aswin C., et al, "CS-MUVI: Video Compressive Sensing for Spatial-Multiplexing Cameras," Proceedings of the IEEE International Conference Computational Photography (ICCP), Apr. 2012, pp. 11. <doi:10.1109/ICCPhot.2012.6215212>.
Zheng, G., et al, "Wide-field, high-resolution Fourier ptychographic microscopy," Nature Photonics, vol. 7, Sep. 2013, Published Online Jul. 28, 2013, pp. 739-746. <doi:10.1038/NPHOTON.2013.187>.
U.S. Appl. No. 15/820,295, filed Nov. 21, 2017, Ou.
Notice of Allowance dated Dec. 4, 2017 in U.S. Appl. No. 14/065,305.
Final Office Action dated Dec. 14, 2017 in U.S. Appl. No. 14/960,252.
Final Office Action dated Dec. 28, 2017 in U.S. Appl. No. 14/710,947.
Supplemental Notice of Allowance dated Dec. 29, 2017 in U.S. Appl. No. 14/065,305.
Final Office Action dated Jan. 17, 2018 in U.S. Appl. No. 14/658,019.
Notice of Allowance dated Jan. 23, 2018 in U.S. Appl. No. 15/206,859.
Office Action dated Jan. 25, 2018 in U.S. Appl. No. 14/065,280.

(56) References Cited

OTHER PUBLICATIONS

Notice of Allowance dated Jan. 26, 2018 in U.S. Appl. No. 15/209,604.
Australian Examination Report/Office Action dated Jan. 18, 2018 issued in AU 2014308673.
Wills, S., "Synthetic Apertures for the Optical Domain," Optics & Photonics News Article [webpage], The Optical Society (OSA), Apr. 18, 2017, pp. 2. <URL:https://www.osa-opn.org/home/newsroom/2017/april/synthetic_apertures_for_the_optical_domain/>.
Office Action Interview Summary dated May 3, 2018 in U.S. Appl. No. 15/068,389.
Office Action dated Apr. 4, 2018 issued in U.S. Appl. No. 15/003,559.
Office Action dated Apr. 13, 2018 issued in U.S. Appl. No. 15/160,941.
U.S. Appl. No. 15/963,966, filed Apr. 26, 2018, Ou et al.
U.S. Appl. No. 15/959,050, filed Apr. 20, 2018, Horstmeyer et al.
Chinese First Office Action dated Feb. 24, 2018 issued in CN 201680003937.1.

FOURIER PTYCHOGRAPHIC RETINAL IMAGING METHODS AND SYSTEMS

CROSS-REFERENCES TO RELATED APPLICATIONS

This application claims priority to U.S. Provisional Patent Application No. 62/137,955, titled "Imaging the Retina of the Eye via Fourier Ptychography" and filed on Mar. 25, 2015, which is hereby incorporated by reference in its entirety and for all purposes.

STATEMENT AS TO RIGHTS TO INVENTIONS MADE UNDER FEDERALLY SPONSORED RESEARCH OR DEVELOPMENT

This invention was made with government support under Grant No. OD007307 awarded by the National Institutes of Health. The government has certain rights in the invention.

FIELD

Certain embodiments described herein are generally related to digital imaging, and more specifically to Fourier ptychographic retinal imaging (FPRI) systems and methods for obtaining a substantially aberration-free, high-resolution image of the retina.

BACKGROUND

High-resolution retinal imaging can significantly improve the quality of diagnosis, disease progression tracking and assessment of therapy in a broad range of retinal diseases including, for example, retinal degenerations (retinitis pigmentosa), macular telangiectasis, macular dystrophies, age-related macular degeneration (AMD), and inflammatory diseases. Some of these diseases are prevalent (AMD afflicts 12% of the population aged 80+, and retinitis pigmentosa is the most common cause of blindness/low-vision in adults 20-60 years old) and progress slowly, which drives the need for a cost-effective imaging solution that can be broadly deployed for screening and tracking purposes. The availability of new therapeutics further drives this need for a cost-effective imaging solution since the ability to discern the exact impact of the drugs at the cell level is highly useful in informing clinicians about the course of treatments.

Accounting for the numerical aperture of the eye as set by a nominal pupil diameter of 6 mm, an imaging system should be able to focus light to a diffraction-limited spot of size of 1.9 microns on the retina (630 nm wavelength) except that aberrations in the eye actually result in a much poorer focus spot. Conventional retinal imaging techniques correct for aberrations by including a corrective physical optical arrangement to compensate for the aberrations before acquiring images. This conventional strategy is the basis of the adaptive optics (AO) work that was first started in astronomy and that has been applied to ophthalmic imaging systems, in particular confocal scanning laser ophthalmoscopes (cSLO). Conventional adaptive optics scanning laser ophthalmoscopes (AOSLO) have significant limitations that have hindered their broad clinical use. First, the field of view of AO corrected images tends to be very small oftentimes only 1 degree in size. Since retinal diseases can occupy large portions of the macula and retina, conventional AO techniques requires multiple images to be obtained and montaged and increases the acquisition time. Long acquisition times are generally impractical for routine clinical use, especially with eye motion from the patient. This requires high-speed tracking systems since AO requires feedback to keep the aberration correction current. Second, the uneven topology of many retinal diseases presents a major challenge because regions not in the focal plane of the optics will appear out of focus. Third, despite reductions in the cost of certain components, such as deformable mirrors, these conventional systems still remain expensive, limiting their commercial feasibility.

SUMMARY

Certain embodiments pertain to Fourier ptychographic retinal imaging (FPRI) systems and methods configured to be able to obtain a substantially aberration-free, high resolution retinal image.

Certain embodiments pertain to Fourier ptychographic retinal imaging methods. In one embodiment, the Fourier ptychographic retinal imaging method comprises focusing on a retina of an eye, illuminating the eye with plane wave illumination, and acquiring a sequence of raw retinal images based on light reflected from the retina. The sequence of raw retinal images is acquired while an aperture passing light to an imaging system is sequentially shifted to different locations at the Fourier plane of an approximate plane of the retina. The method further comprises, after acquiring the raw retinal images, reconstructing a complex full resolution image of the retina with phase and amplitude image data recovered by iteratively updating regions in Fourier space with data from the plurality of raw retinal images and correcting aberration in the reconstructed complex full resolution image of the retina to generate a substantially aberration-free, full resolution retinal image.

In one embodiment, the Fourier ptychographic retinal imaging method comprises receiving a sequence of raw retinal images of a retina of an eye from an imaging system. The sequence of raw retinal images is acquired by one or more image sensors of the imaging system, wherein the sequence of raw retinal images is based on light reflected from the retina while an aperture modulator sequentially shifts an aperture to different locations at the Fourier plane of an approximate plane of the retina and while an illumination source provides plane wave illumination propagated to the eye through an optical system. The method further comprises reconstructing a complex full resolution image of the retina with phase and amplitude image data recovered by iteratively updating regions in Fourier space with data from the plurality of raw retinal images and correcting aberration in the reconstructed complex full resolution image of the retina to generate a substantially aberration-free, full resolution retinal image.

Certain embodiments pertain to Fourier ptychographic retinal imaging systems. In one embodiment, a Fourier ptychographic retinal imaging system for imaging a retina of an eye comprises an illumination source configured to provide plane wave illumination, an aperture modulator configured to sequentially shift an aperture to different locations at the Fourier plane of an approximated plane of the retina, and an imaging system with one or more image sensors configured to acquire a sequence of raw retinal images based on light reflected from the retina. The system further comprises an optical system for propagating the plane wave illumination to the eye and for propagating light reflected from the retina to the imaging system and a processor in communication with the imaging system to receive a signal with data of the plurality of raw retinal images from the imaging system. The processor configured to reconstruct a complex full resolution image of the retina with phase and amplitude image data recovered by iteratively updating regions in Fourier space with data from the plurality of raw retinal images, wherein the processor is further configured to correct aberration in the complex full resolution image to generate a substantially aberration-free, full resolution image of the retina.

These and other features are described in more detail below with reference to the associated drawings.

DETAILED DESCRIPTION

Figure 1:
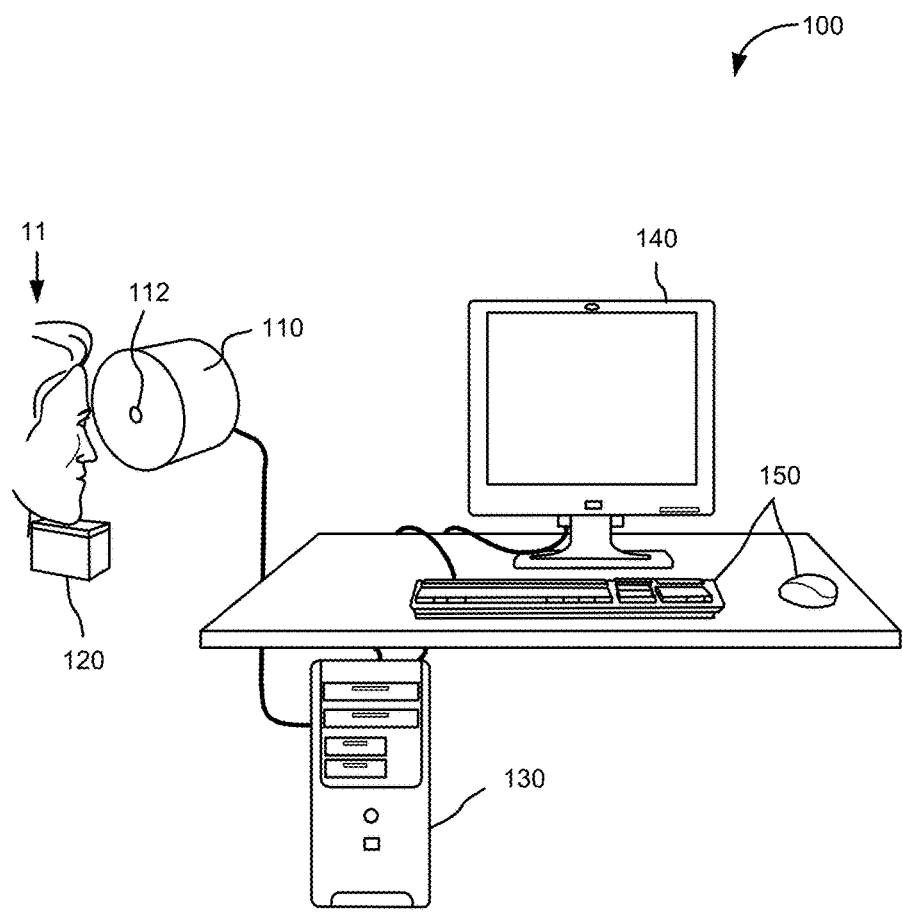
FIG. 1 is a schematic diagram of a FPRI system capable of implementing an FPRI method, according to embodiments.

Certain embodiments pertain to Fourier ptychographic retinal imaging (FPRI) methods and systems for obtaining a substantially aberration-free, high-resolution image of the retina. Some of these embodiments are described below with reference to the accompanying drawings. The features illustrated in the drawings may not be to scale in some instances.

I. Introduction

Conventional AO retinal imaging methods physically characterize the inherent optical aberrations of the eye, and modulate the imaging system to correct for these aberrations before image acquisition. The FPRI methods and systems described herein use a significantly different strategy for achieving high-resolution retinal images. The FRPI methods and systems collect a sequence of raw retinal images in which optical aberrations are present, computationally determine the aberrations, and then titrate the raw images into a high-resolution retinal image. This may beneficial because the aberration correction can be done after the image capturing process, unlike the conventional AO systems which require the aberration to be corrected for within the image acquisition procedure which extends the examination time and could become uncomfortable for the patient. Also, the mechanical components involved in conventional AO imaging systems are typically expensive.

In certain embodiments, the FPRI system comprises an illumination source for providing plane wave illumination, an imaging system (e.g., digital camera) with image sensor(s) configured to acquire a sequence of relatively low resolution (raw) images of the retina, an optical system configured to propagate the plane wave illumination from the illumination source to the retina and propagate light reflected from the retina to the imaging system, an aperture modulator (e.g., spatial light modulator) for quickly shifting a transmissive (reflective) aperture to N different regions across the Fourier plane of the retina, and one or more processors for processing the raw low-resolution images to generate a substantially aberration-free, high-resolution retinal image. The optical system is generally configured to generate intensity distributions of the reflected light from the retina at the image sensor(s) and has an optical arrangement (e.g., 4f arrangement or a 6f arrangement) that allows the aperture modulator to modulate the image's spatial spectrum providing a shifting aperture at the Fourier plane of the retina. In some cases, the raw images collected by the imaging system are based on reflection geometry of the optical system such as shown in the optical system in FIG. 2. In some embodiments, the aperture modulator is an SLM that can be digitally addressed to quickly shift the aperture across the Fourier plane.

In an exemplary method, the FPRI system first focuses at the approximate plane of the retinal layer. This first operation may involve locating the eye (e.g., by placing person's head on a stationary neck rest) such that the retina is in focus. In addition or alternatively, the optical system may include components that focus the retina of the eye. Next, a controller sends signals to the illumination source, to the imaging system, and to the aperture modulator to synchronize capturing of a sequence of raw images of the retina while the aperture modulator generates apertures (also called windows) at different locations at the Fourier plane and while the illumination source provides plane wave illumination. In some cases, the illumination source provides pulses of light (e.g. pulses with pulse duration of about 0.1 ms) to help reduce motion artifacts during the raw image acquisition procedure. In these cases, the imaging system (e.g., high-speed digital camera) is synchronized so that the exposure times for capturing the raw images coincide with the pulses.

Components of the optical system such as, for example, a polarized beam splitter and/or a quarter wave plate, are placed in front of the eye to propagate plane wave illumination from the illumination source to the eye. The retina at the back of the eye reflects light out of the eye and the optical system collects and propagates the reflected light to the imaging system. The imaging system (e.g., high-speed digital camera) acquires a sequence of raw images of the retina while the aperture modulator (e.g., SLM) selectively blocks different areas of the light field entering into the pupil plane of the image sensor(s) of the imaging system. During the raw image acquisition process, a sequence of N raw images is acquired where N is the number of total shifted aperture (window) locations. In the case where the aperture modulator is an SLM, N is the number of total shifted SLM admittance functions.

Each raw image captured by the imaging system is generally a unique, poorly-resolved measurement of the retinal surface. Both the inherent optical aberrations of the eye, as well as the finite passband of the shifting aperture, limit their achievable resolution. The FPRI method transforms this low-resolution image sequence into a high-resolution amplitude and phase map. Subsequently, the FPRI method uses this phase map to determine the optical aberrations of the eye's media (e.g., cornea, aqueous, lens, and vitreous) by appropriately gating the spatial frequency components.

Optical aberrations of the eye's media can be fully characterized by a set of phase distortions that perturb incident light at the pupil plane (not the actual eye's pupil, but the optical definition of pupil). These phase distortions can be summarized using a complex pupil function, typically defined as a finite sequence of Zernike polynomials. In conventional AO-based retinal imaging methods, an external optical system is used to measure and then actively correct (i.e., optically flatten) this pupil function prior to acquiring images of the retina. The FPRI method instead collects a raw image sequence through the uncorrected pupil function, and then corrects any distortions after raw image acquisition. The FPRI method uses an improved version of the Fourier Ptychographic (FP) phase retrieval process. The conventional FP phase retrieval process could be used to reconstruct the complex function of the incident light using a phase retrieval process. The complex function in this case is a combination of the sample's distribution and the optical system's aberrations. The improved version of the FP techniques includes a phase retrieval process that reconstructs the pupil function of the representative optical system of the eye (i.e. the aberration induced by elements between the plane of interest and the imaging sensor) and the wavefront information of light reflected from the eye (i.e. the complex function of the plane of interest). That is, the FPRI method determines and corrects the aberration of the specimen outside the FPRI system that is introduced before/at the image acquisition procedure. Consequently, the plane of interest, in this case the retina, is clearly resolved with the aberrations removed. The FPRI method uses this improved version of the FP techniques to generate a high-resolution retinal image by mathematically "flattening" the eye's unknown aberrated pupil function and stitching different low-passed wavefronts in the spatial frequency domain. Details of conventional Fourier ptychographic techniques with phase retrieval can be found in G. Zheng, R. Horstmeyer, and C. Yang, "Wide-field, high-resolution Fourier ptychographic microscopy," Nat. Photonics, vol. 7, no. 9, pp. 739-745 (July 2013), which is hereby incorporated by reference in its entirety.

As discussed, the FPRI methods and systems can reconstruct an aberration-free image of the retina. In certain embodiments, a sequence of raw images is captured within the time frame of the eye's movement by illuminating the retina with an illumination source and shifting a small aperture to different locations at the Fourier plane of the approximate retinal plane using an aperture modulator (e.g., SLM). The raw images are stitched together with Fourier ptychography (FP) techniques to generate a high-resolution, complex image containing the image of retina and the optical aberrations of the eye. The aberrations are separated from the retinal image by appropriately gating the spatial frequency components of the complex image. Details of the conventional FP techniques are described in G. Zheng, R. Horstmeyer and C. Yang, "Wide-field, high-resolution Fourier ptychographic microscopy," Nature Photonics (2013), in U.S. patent application Ser. No. 14/065,280, titled "FOURIER PTYCHOGRAPHIC IMAGING SYSTEMS, DEVICES, AND METHODS" and filed on Oct. 28, 2013, and in U.S. patent application Ser. No. 14/466,481, titled "VARIABLE-ILLUMINATION FOURIER PTYCHOGRAPHIC IMAGING DEVICES, SYSTEMS, AND METHODS" and filed on Aug. 22, 2014, which are all hereby incorporated by reference in their entirety.

In one embodiment, the FPRI method includes a simulated annealing process applied on the reconstructed complex image to separate the retinal image and the optical aberrations of the eye by modeling the aberrations as a combination of Zernike polynomials. An aberration-free retinal image is produced as a result of the simulated annealing process. Details of the simulated annealing process can be found in R. Horstmeyer, X. Ou, J. Chung, G. Zheng and C. Yang, "Overlapped Fourier coding for optical aberration removal," Optics Express, 2014, which is hereby incorporated by reference in its entirety.

Some embodiments of the FPRI methods and systems may provide one or more technical advantages. For example, certain embodiments of the FPRI methods and systems can correct for the optical distortions of the eye after raw image acquisition which provides a simpler (simpler to use and simpler optics) and less expensive scheme than conventional AO-based methods. In addition, since the FPRI methods and systems perform aberration correction post-acquisition, the FPRI method is robust since the aberration correction process and image acquisition process are separated. Aberration correction can be done and the image rendering can be finessed at a later time after image acquisition, without imposing additional time on the patient during the acquisition process. Also, certain embodiments of the FPRI methods and systems can be used to refocus the corrected image after image acquisition, which also allows for the ability to generate a topological profile of the retina. The refocusing can be done digitally by propagating the complex sample function to different planes and finding the plane with the sharpest contrast in the image. The location of such plane represents the topological height of that region; doing this for multiple regions in the retina can generate the topological map of the retina. Since the FPRI method produces both phase and intensity image data, the phase data can be used to render phase contrast images of the retina to provide better contrast, as is often done for angiographies.

II. FPRI Systems

FIG. 1 is a schematic diagram of a FPRI system 100 capable of implementing an FPRI method, according to embodiments. At a high level, the FPRI system 100 is configured or configurable to illuminate the retina of an eye to capture a sequence of raw retinal images during a raw image acquisition process, process the raw image data to reconstruct a full resolution complex image of the retina and use an aberration correction process to correct the aberration in the complex image to generate a substantially aberration-free or aberration-free complex image of the retina. For illustration purposes, the FPRI system 100 is shown with a person 11 positioned during the raw image acquisition process.

The FPRI system 100 includes an opaque casing 110 that contains components of the FPRI system 100 including, for example, an illumination source, an optical system, and an imaging system. The opaque casing 110 has a transparent region 112 for allowing illumination from the illumination source inside the casing 110 to illuminate the retina of the eye of the person 11. The casing 110 is shown here in the shape of a cylinder with a circular transparent region 112 for simplicity. Other shapes can be used for the casing and/or the transparent region 112. The transparent region 112 may be made of a transparent material or may be a hole.

The FPRI system 100 is also shown with an optional rest 120 for positioning the person 11 so that the optical system is generally focused at the approximate plane of the retinal layer of the eye of the person 11. The optional rest 120 can also help stabilize or prevent movement of the person 11 during the raw image acquisition process. In some cases, the optical system may include a lens that can be moved to more accurately focus the optical system at the approximate plane of the retinal layer at the back of the eye of the person 11.

The casing 110 may be mounted to the wall or placed on or mounted to a platform such as a desk, a stand, or a chair for receiving the person 11. The rest 120 may be mounted to the same object as the casing 110 or another object.

The FPRI system 100 also includes a computing device 130 having one or more processors and a computer readable medium (CRM), e.g., memory, in electronic communication with the one or more processors. The one or more processors execute instructions stored on the CRM to complete operations of an FPRI method. The FPRI system 100 also includes a display 140 and one or more input devices 150 (e.g., keyboard and mouse), both of which are in electronic communication with the computing device 130. The components of the FPRI system 100 inside the casing 110 are in electronic communication with the computing device 130 via wiring. In this example, many of the components of the FPRI system 100 are in electronic communication to each other via wiring. It would be understood that the electronic communication between components of the FPRI systems described herein can be in wired form, wireless form, or a combination thereof.

Output from operations of the FPRI method such as an aberration-free or substantially aberration-free, high-resolution image of the retina can be displayed on a display of the FPRI system. An example of such a display 140 is shown in FIG. 1. In this example, the one or more processors of the computing device 130 execute instructions stored on the CRM to generate display data of output of the FPRI method. The one or more processors send a signal with the display data to the display 140 to display the output from the FPRI method.

In one aspect, after operation 360, the ACIS imaging method further comprises sending a signal with display data from the processor(s) to a display to display the improved resolution bright-field image, aberration-corrected fluorescence image(s), and other data generated by the ACIS imaging method.

The FPRI imaging system 100 includes an illumination system 102, an optical system 106, and an image sensor system 108. A controller 110 controls operations of the ACIS imaging system 100 based on instructions stored in memory and/or provided by an operation of the ACIS imaging system 100. The controller 110 is in electrical communication with the image sensor system 108 to receive the raw image data from the image sensor system 108. Optionally (denoted by dotted lines), the controller 110 is in electrical communication with the illumination system 102 to control the illumination from this system, for example, in order to synchronize the illumination with the exposure times during acquisition of raw images (bright-field and/or fluorescence) by the image sensor system 108. The controller 110 or another processor controls the illumination from light sources of the illumination system 102, for example, by selectively powering on or otherwise allowing only particular ones or subsets of the light sources to form various illumination patterns at particular times and for particular durations during various image acquisition exposures. In some implementations, the controller 110 is further configured to execute instructions to perform processing operations on the raw image data such as operations performed as part of the ACIS imaging method.

According to certain embodiments, an FPRI system has an imaging system configured or configurable for high-speed capturing of a sequence of raw images of the retina. For example, the imaging system may be configured to acquire raw images at about 200 frames/second. In another example imaging system may be configured to acquire raw images at about 100 frames/second. In another example imaging system may be configured to acquire raw images at about 500 frames/second. An example of a suitable imaging system is a high-speed digital camera such as a Fast Frame Rate CCD Camera (e.g., Thorlabs 340M-CL). In one embodiment, the imaging system is configured to acquire raw images in a range of about 200 frames per second-500 frames per second.

Generally, the imaging system of an FPRI system has one or more imaging sensors. According to certain implementations, the one or more image sensors are configured to capture light and output a data signal including image data representative of the intensities of light received at particular locations of the image sensor(s) (referred to herein as a "light intensity distribution," "intensity distribution," or simply as an "image"). The image data output by each image sensor is transmitted (or "sent" or "communicated") to one or more processors of the FPRI system.

In certain embodiments, the image sensor(s) of an FPRI system is configured to acquire a sequence of N raw intensity images of a field of view of the retina during a raw image acquisition process. The image sensor(s) acquire a raw image by measuring an intensity distribution of light incident the sensing area of the image sensor(s) during an exposure time. Some examples of suitable image sensors are CMOS sensors, a charge-coupled device (CCD), and other similar imaging devices. In one example, an image sensor is a CMOS having a pixel size 11 μm such as the pco dimax HS4. In one embodiment, each image sensor is a monochromic light detector.

The processor(s) of the FPRI system are configured to interpret and process raw image data from its raw image acquisition processes to generate processed image data. In some implementations, the processor(s) of the FPRI system are configured or configurable by a user to perform Fourier ptychographic operations on the raw image data of a sequence of intensity images to reconstruct a full resolution complex image of the field of view of the retina. In these cases, the one or more processors interprets the image data from the sequence of intensity images, transforms the relatively low-resolution image data images into Fourier space, combines the transformed raw image data, and reconstructs the amplitude and phase data for a high-resolution complex image of the field of view of the retina. The one or more processors also interpret the image data to use an aberration correction process to correct the aberration in the complex image to generate a substantially aberration-free or aberration-free complex image of the field of view of the retina.

During the raw image acquisition procedure, an illumination source provides plane wave illumination to the retina via one or more components of the optical system. Generally, the illumination source of embodiments is a monochromatic light source providing spatially coherent light. Some examples of suitable illumination sources include a collimated LED and a laser. An example of a suitable illumination source is a high intensity LED at 630 nm wavelength.

In certain embodiments, the illumination source is configured to generate a sequence of pulsed light. The pulsed light helps reduce motion artifacts during the raw image capturing process. In one case, the pulse duration is about 0.1 ms. In another case, the pulse duration is about 0.2 ms. In another case, the pulse duration is a range of about 0.01 ms to 0.2 ms. The pulse can be created, for example, by guiding the light through an acousto-optic modulators (AOM) which modulates the light (e.g. LS110A-VIS-XY from ISOMET), or by using an optical chopper (e.g. Thorlabs's MC1F2) to allow light to pass only for a short duration.

As used herein, an aperture modulator refers to a device that can be configured to quickly shift a transmissive (reflective) aperture(s) to N different locations across the Fourier plane of the retina. In some embodiments, the number of aperture locations N has a value in a range of 1 to about 2000. In one case, the number of aperture locations N is about 200. In one case, the number of aperture locations N has a value in the range of 1 to about 200. In another case, the number of aperture locations N has a value in the range of 1 to about 3000. In another case, the number of aperture locations N has a value in the range of 200 to 1000. The shape of the aperture generated by the aperture modulator varies. In some cases, the shape is rectangular with dimensions of width l and height h. In other cases, the shapes are circular shape with radius r. In other cases, the shapes are triangular. In one case, the aperture modulator is configured to shift the transmissive (reflective) aperture(s) to N different locations in 1 second. In one case, the aperture modulator is configured to shift the transmissive (reflective) aperture(s) to N different locations in 0.5 seconds. In one case, the aperture modulator is configured to shift the transmissive (reflective) aperture(s) to N different locations in 0.1 seconds.

The aperture modulator may be in different forms. Some examples of suitable forms of aperture modulator devices that can be used in the FPRI systems of embodiments include, for example, a spatial light modulator (SLM), a reflective liquid-crystal on silicon (LCoS) display, a digital micromirror device (DMD), and the like. Although certain embodiments of the FPRI system are described with an aperture modulator configured to generate a single aperture at different locations during the image acquisition process, the disclosure is not so limiting. For example, the aperture modulator may be configured to generate different sizes of apertures at different image acquisition times or may be configured to generate unique patterns of multiple apertures at different image acquisition times.

In certain embodiments, the aperture modulator is in the form of an SLM that can be digitally addressed to quickly shift a transmissive (reflective) aperture(s) across its display located at the Fourier plane of the retina. An example of a suitable SLM is the Holoeye LC-R 720. The SLM uses an electrical and/or optical signal from an SLM light source to modulate phase, $\varphi$, and/or amplitude of light. In some cases, the SLM light source may be a collimated light source such as a laser (e.g., Excelsior® 532 SM). In other cases, the SLM light source may not be collimated light. For example, the light may be spatially filtered light from a light emitting diode (spatial coherence length of approximately 1 mm, spectral bandwidth of 20 nm), or light from a laser source (e.g., 532 nm quasi-monochromatic laser light, spatial coherence length of multiple meters).

Generally an SLM comprises an SLM display with discrete display elements. Each discrete SLM element can be set to function as an aperture (aperture setting) or to function as the area surrounding the aperture (field setting). In some configurations, an SLM display element in an aperture setting is transparent or nearly transparent to pass incident light and a display element in a field setting may block/reflect or nearly bock/reflect incident light. In other configurations, certain SLM display elements may be reflective. In these cases, a display element in the aperture setting is oriented at a (first) angle to reflect incident light to the next optical element in the optical arrangement and a display element in a field setting is oriented at a different (second) angle that reflects incident light away from the next optical element. In these configurations, the SLM display can generate an aperture at one or more SLM display elements by setting these display elements in an aperture setting and/or setting the surrounding display elements in a field setting. At different raw image acquisition times, $t_i$, different sets of one or more display elements are at appropriate settings to generate the aperture at the corresponding aperture location. In one case, the SLM display may have a refresh rate in the range of 30 per second to 100 per second. In another case, the SLM display may have a refresh rate in the range of 100 per second to 200 per second.

In certain embodiments, the aperture modulator is the form of an LCoS display. The LCoS display is a reflective display having a plurality of reflective display elements. An example of a commercially available LCoS display is the reflective HOLOEYE® SLM, Pluto, phase only LCoS, 8 μm pixel size, 1080×1920 pixels display.

In certain embodiments, the aperture modulator is the form of a DMD. The DMD comprises an optical semiconductor chip having on its surface multiple microscopic micromirrors. In certain aspects, each micromirror can be individually rotated to an angle, $\alpha$. In this way, each micromirror can be transitioned to either an aperture setting at angle, $\alpha$, or to a field setting at no rotation, or visa versa. Although these micromirrors are usually arranged in a rectangular array (dimensions o×p), other arrangements may be used. In certain aspects, each micromirror of the DMD may correspond to one or more light detector pixels. In one case, one or more of the micromirrors in the aperture setting may be oriented so that an optical axis orthogonal to the surface of the micromirror is oriented at an angle, $\alpha$, from the Fourier plane.

The FPRI system has an optical system that is generally configured to propagate illumination from the illumination source to the retina and to propagate reflected light from the retina to the one or more image sensors to be able to capture the raw images of the retina. The optical system is also configured with an optical arrangement, e.g., 4f arrangement, that will allow for the modulation of the images image's spatial spectrum using an aperture modulator that modulates an aperture(s) at the Fourier plane of the retina, typically in a reflection geometry. An example of components of an optical system that can be included in an FPRI system of embodiments is provided in FIG. 2.

Figure 2:
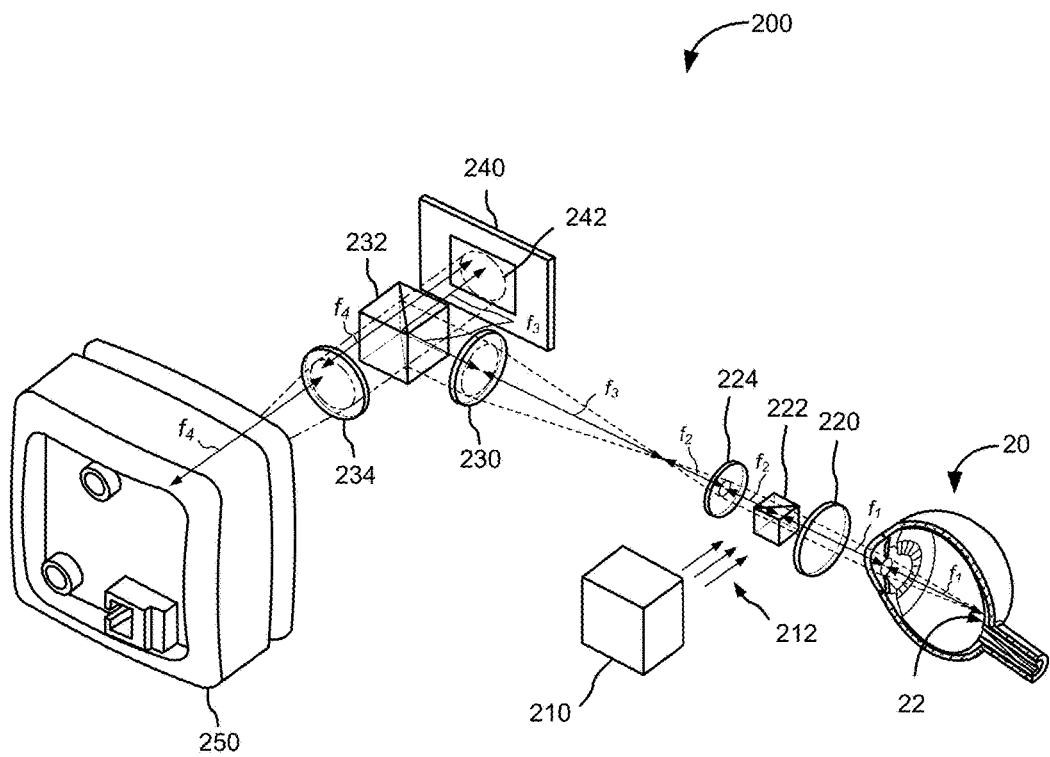
FIG. 2 is a schematic diagram of an FPRI system capable of implementing an FPRI method, according to embodiments.

FIG. 2 is a schematic diagram of components of an FPRI system 200, according to embodiments. The FPRI system 200 comprises an illumination source 210 (e.g., an LED) for providing plane wave illumination 212, an optical system, an aperture modulator 240, and an imaging system 250. The optical system includes components for propagating illumination from the illumination source 210 to the eye 20. The optical system also includes components for propagating light reflected from the retinal surface 22 and passing out the eye 22 to the imaging system 250.

The optical system comprises the optional components of a quarter wave plate 220 and a first polarizing beam splitter 222 located in front of the eye 20. The first polarizing beam splitter 222 is designed to reflect the component of the light with a particular polarization direction (e.g. 0 degrees) while transmitting the component with the perpendicular polarization direction (e.g. 90 degrees). In the illustrated example, illumination source 210 is shown activated and providing unpolarized plane wave illumination 212 to the first polarizing beam splitter 222. The first polarizing beam splitter 222 reflects a particular polarization component of the incident unpolarized plane wave illumination 212 in a direction that is substantially perpendicular to the front surface of the quarter wave plate 220. The quarter wave plate 220 rotates the polarization of the reflected light from the first polarizing beam splitter 222 by 45 degrees and direct it to the eye 20. The polarized light propagates through the eye's media (e.g., cornea, aqueous, lens, and vitreous) and is reflected from the retinal surface at the back of the eye 20. The reflected light from the retinal surface is propagated back through the eye's media and to the quarter wave plate 220. The quarter wave plate 220 receives the reflected light from the retinal surface and further rotates its polarization by 45 degrees, making its polarization transmissible by the first polarizing splitter 222. The first polarizing beam splitter 222 receives the light from the quarter wave plate 220 and passes reflected light from the retinal surface. In other embodiments, one or more of these optional components are not included. Examples of suitable polarizing beam splitters and quarter wave plates are commercially available.

The optical system also comprises a first lens 224, a second lens 230, a second polarizing beam splitter 232, and a third lens 234. The optical system is in a 6f arrangement where the first lens 224 has a focal length, $f_2$, and the eye 20 is located so that the Fourier plane of the retina is $f_2$ away from the first lens. The focal length $f_1$ is the approximate focal length of the lens of the eye 20. The reflected light from the retinal surface of the first polarization is passed through the first polarizing beam splitter 222 to the first lens (e.g., objective lens) and to the second lens 230. The second lens 230 is a lens with focal length $f_3$. The second lens 230 reflects light passed by the second lens 230 to the aperture modulator 240. Light incident the aperture modulator 240 within the admittance circular pupil function 240 will be reflected to and transmitted through the second polarizing splitter 232 and through the third lens 234. The third lens 234 is a focusing lens with a focal length $f_4$. The third lens 234 focuses the light passed by the second polarizing beam splitter 232 to the one or more imaging sensors of the imaging system 250.

During an exemplary image acquisition process of the FPRI system 200, the eye 20 is positioned in front of the first polarizing beam splitter 222 and the quarter wave plate 220 or the first polarizing beam splitter 222 and the quarter wave plate 220 are positioned in front of the eye 20. The illumination source (e.g., LED) 210 receives control signals to turn on to provide plane wave illumination 212. In some cases, the illumination source 210 provides a sequence of pulsed light to help reduce motion artifacts during the image capturing. Control signals are sent to the imaging system 250 to synchronize image acquisition with illumination. In cases with pulsed light, control signals are sent to the imaging system 250 to capture images that coincide with the pulses.

The light from the retina propagates to the retinal focal length away from the pupil, essentially being Fourier transformed. This Fourier transformed field of the retina is relayed to the aperture modulator by the telescope with focal lengths $f_2$ and $f_3$, with the associated magnification given by the ratio of $f_3$ to $f_2$. The aperture modulates how much of the Fourier spectrum is transmitted to the camera.

The aperture modulator 240 generates an admittance circular pupil function 242 (also referred to as a window or an aperture) that will be sequentially translated in step increments to different locations across the Fourier plane of the approximate retinal plane. In one example, the aperture modulator 240 generates a 1 mm diameter admittance circular pupil function 242 and sequentially translates it in step increments of 0.3254 mm in a square grid pattern. Other diameters, step increments and patterns may be used. Generally the adjacent pupil function regions in the Fourier plane overlap by at least a particular amount such as, for example, at least 60%, at least 65%, at least 70%, or at least 75%. In one embodiment, the overlap is adjusted to improve convergence of the FPRI method. The imaging sensor 250 captures a sequence of raw images of the retina while the aperture modulator 240 selectively blocks different areas of the light field entering into the pupil plane of the imaging system 250. Each raw image is a unique, poorly resolved measurement of the retinal surface. Both the inherent optical aberrations of the eye, as well as the finite passband of the shifting aperture, limit their achievable resolution. The FPRI method uses the FP technique schematically illustrated in FIG. 3 to extract both phase and amplitude information of the wavefront emerging from the eye 20. The FP technique also fuses the raw image data into a full-resolution complex image by overlapping Fourier data. The FPRI method uses a simulated annealing process applied on the complex image to separate the retinal image and the optical aberrations of the eye by modeling the aberrations as a combination of Zernike polynomials. An aberration-free retinal imaging is produced as a result. Details of the overlapped Fourier coding technique can be found in R. Horstmeyer, X. Ou, J. Chung, G. Zheng and C. Yang, "Overlapped Fourier coding for optical aberration removal," Optics Express, 2014, which is hereby incorporated by reference in its entirety.

Figure 3:
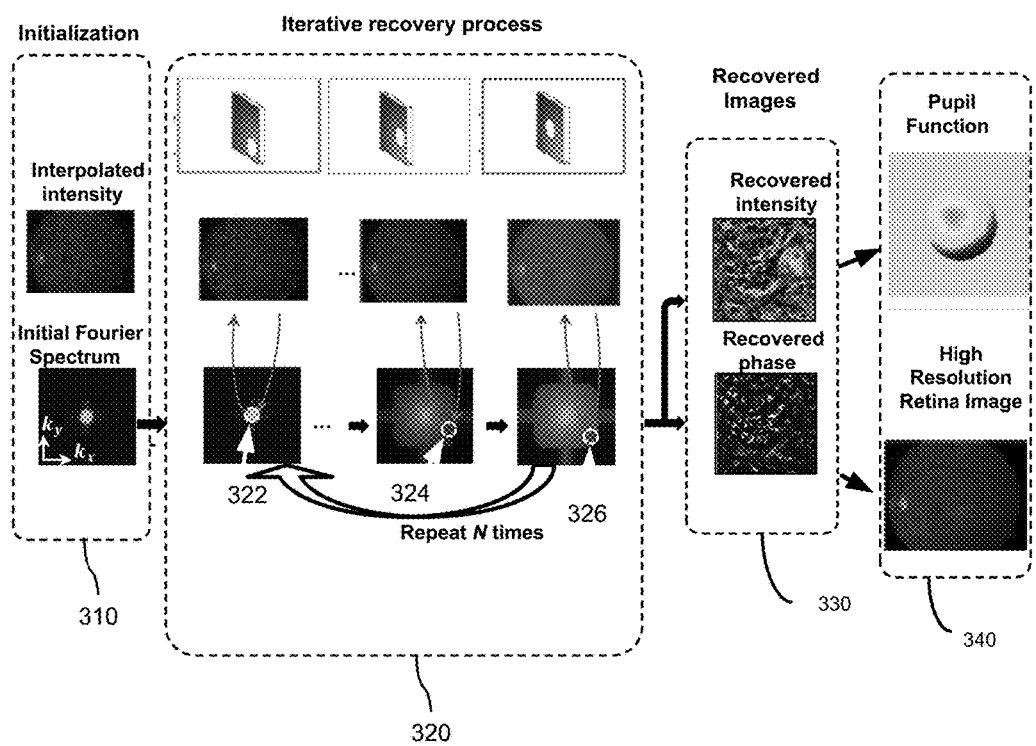
FIG. 3 is a schematic drawing of certain operations of a FP technique, according to embodiments.

FIG. 3 is a schematic drawing of certain operations of a FP technique, according to embodiments. The schematic drawing includes illustrations 310, 320, 330 and 340. Illustration 310 includes a representative image of an initial spectrum and the interpolated intensity. Illustration 320 represents the iterative portion completed for all N raw images. Each of the regions 322, 324, and 326 are the circular low-pass filter shapes in Fourier space of the high-resolution solution. The corresponding low-passed images, as displayed in the center row, are used to update the filtered regions of the high-resolution image's spectrum. The dimensions of these regions are defined by aperture size generated by the aperture modulator. Illustration 330 includes the recovered phase image and the recovered intensity images. Illustration 340 includes the recovered pupil function and the high-resolution substantially aberration-free complex retina image, titrated from the complex reconstructed image.

In certain embodiments, the optical system of the FPRI system has one or more beam-splitters. Each beam splitter is configured to reflect half of the light and transmit the other half. In certain embodiments, the beam-splitter is polarizing (i.e. a polarizing beam splitter) which reflects the light with a particular polarization direction and transmits the light with the perpendicular polarization. In one example, the beam-splitter is a half-silvered mirror with a continuous thin coating of reflective material (e.g., metal). In one example, the polarizing beam splitter is a fused glass with dielectric coating in the fusing junction. In another example, the polarizing beam splitter is a thin glass with dielectric coating on the surface.

Figure 4:
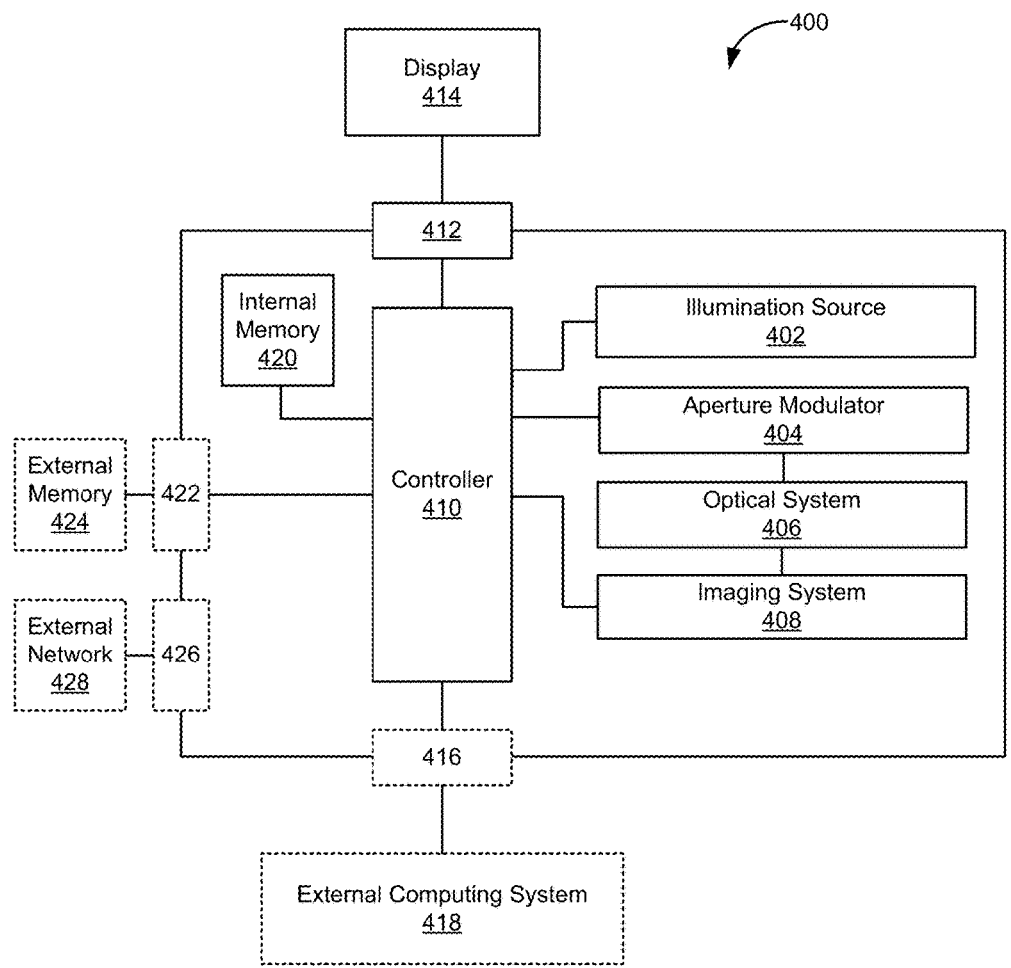
FIG. 4 is a schematic diagram of an FPRI system capable of implementing an FPRI method, according to embodiments.

FIG. 4 is a block diagram of an FPRI system 400 capable of implementing an FPRI method, according to some implementations. At a high level, the FPRI system 400 is configured or configurable to illuminate a retina with plane wave illumination, shift an aperture to different positions at the Fourier plane of the retina, and capture a sequence of raw images of the retina. For example, the FPRI system 400 may be configured or configurable to activate an illumination source 402 to provide pulses of plane wave illumination. The described communication between components of the FPRI system 400 may be in a wired form and/or wireless form.

The FPRI system 400 includes an illumination source 402, an aperture modulator 404, an optical system 406, and an imaging system 408. The FPRI system 400 also includes a controller 410 comprising one or more processors and a CRM (e.g., memory) in electronic communication with the one or more processors. The controller 410 controls operations of the FPRI system 400 based on instructions stored on memory and/or provided by an operation of the FPRI system 400. The controller 410 is in electrical communication with the imaging system 408 to receive the raw image data. The controller 410 is also in electrical communication with the illumination source 402 to control the timing of the illumination, for example, in order to synchronize pulses of illumination with the exposure times of the raw images by the imaging system 408. The controller 410 controls the illumination from light sources of the illumination source 402, for example, by selectively powering on the illumination source during image acquisition exposures. The controller 410 is also in electrical communication with the aperture modulator 404 to shift the aperture to different locations to synchronize the locations with the illumination and exposure times of the raw images by the imaging system 408. In some implementations, the processor(s) of the controller 410 are further configured to execute instructions to perform processing operations on the raw image data such as operations performed as part of the FPRI method.

The imaging system 408 is in communication with the optical system 406 to receive light from the optical system 406 and capture raw images, each raw image captured over an exposure time. The illumination source 402 is in communication with the optical system 406 to provide illumination to a sample being imaged such that light scattered by or otherwise issuing from the sample is propagated through the optical system 406 to the imaging system 408 which captures raw images.

During raw image acquisition, light generated by the illumination source illuminates the retina with plane wave illumination. Light reflected from the retina is propagated through the optical system 406 to the imaging system 408 which captures a sequence of raw images of the retina. The aperture modulator 404 is in communication with the optical system 406 to shift a circular pupil function to different locations across the Fourier plane of the retina in order to selectively block different areas of the light field entering into the pupil plane of the imaging system.

The imaging system 408 has one or more image sensors. According to certain implementations, an image sensor is configured to capture light and output a data signal including image data representative of the intensities of light received at particular locations of the image sensor (referred to herein as a "light intensity distribution," "intensity distribution," or simply as an "image" or "image frame"). The image data output by each image sensor is transmitted (or "sent" or "communicated") to a processor of, for example, a controller. The image sensor(s) of an FPRI system can acquire a sequence of N raw intensity images during the image acquisition process. Each image sensor acquires a raw image by measuring an intensity distribution of light incident the sensing area of image sensor during an exposure time. Some examples of suitable image sensors are CMOS sensors, a charge-coupled device (CCD), and other similar imaging devices. In certain implementations, the one or more image sensors in an FPRI system are monochromic light detectors. In certain embodiments, the imaging system is camera. An example of a suitable camera is the pco.imax HS4 (made by PCO.edge) which comprises a CMOS sensor with a pixel size of 11 µm.

The controller 410 is configured to interpret and process raw image data from the imaging system 408 to generate processed image data. In some implementations, the controller 410 is configured or configurable by a user to perform FP processing operations on the raw image data of a sequence of the intensity images. In these cases, the controller 410 interprets image data from the sequence of acquired intensity images, transforms the relatively low-resolution image data frames into Fourier space, combines the transformed raw image data, and reconstructs amplitude and phase data for a single complex high-resolution image of the retina. In some cases, the controller 410 uses the amplitude and phase data to determine aberrations due to components of the eye and correct the aberrations in the complex high-resolution image. The controller 410 can also generally include functionality to interpret and process the raw image data captured during each image acquisition process to generate substantially aberration-free image of the retina.

According to certain implementations, the controller 410 can perform parallel image processing. To perform parallel image processing, the controller 410 generally includes at least one processor (or "processing unit"). Example processors include, for example, one or more of a general purpose processor (CPU), an application-specific integrated circuit, an programmable logic device (PLD) such as a field-programmable gate array (FPGA), or a System-on-Chip (SoC) that includes one or more of a CPU, application-specific integrated circuit, PLD as well as a memory and various interfaces. The controller 410 also is in communication with at least one internal memory device 420. The internal memory device 420 can include a non-volatile memory array for storing processor-executable code (or "instructions") that is retrieved by the processor to perform various functions or operations described herein for carrying out various algorithms or other operations on the image data. The internal memory device 420 also can store raw and/or processed image data (including FP-reconstructed images and aberration free images of the retina). In some implementations, the internal memory device 420 or a separate memory device can additionally or alternatively include a volatile memory array for temporarily storing code to be executed as well as image data to be processed, stored, or displayed. In some implementations, the controller 410 itself can include volatile and in some instances also non-volatile memory.

In some implementations, the controller 410 is configured or configurable by a user to output raw image data or processed image data over a communication interface 412 for display on a display 414. In some implementations, the controller 410 also can be configured or configurable by a user to output raw image data as well as processed image data over an optional (denoted by dotted line) communication interface 416 to an optional (denoted by dotted line) external computing device or system 418. Indeed in some implementations, one or more of the FPRI operations can be performed by such an external computing device 418. In some implementations, the controller 410 also can be configured or configurable by a user to output raw image data as well as processed image data over an optional (denoted by dotted line) communication interface 422 for storage in an optional external memory device or system 424. In some implementations, the controller 410 also can be configured or configurable by a user to output raw image data as well as processed image data over an optional (denoted by dotted line) network communication interface 426 for communication over an optional (denoted by dotted line) external network 428 (for example, a wired or wireless network). The network communication interface 426 also can be used to receive information such as software or firmware updates or other data for download by the controller 410. In some implementations, the FPRI system 400 further includes one or more other interfaces such as, for example, various Universal Serial Bus (USB) interfaces or other communication interfaces. Such additional interfaces can be used, for example, to connect various peripherals and input/output (I/O) devices such as a wired keyboard or mouse or to connect a dongle for use in wirelessly connecting various wireless-enabled peripherals. Such additional interfaces also can include serial interfaces such as, for example, an interface to connect to a ribbon cable. It should also be appreciated that one or more of the variable coherent illumination source, the illumination source, and the imaging system 408 can be electrically coupled to communicate with the controller 410 over one or more of a variety of suitable interfaces and cables such as, for example, USB interfaces and cables, ribbon cables, Ethernet cables, among other suitable interfaces and cables.

The data signals output by the image sensors of an imaging system may in some implementations be multiplexed, serialized or otherwise combined by a multiplexer, serializer or other electrical component of the imaging system before being communicated to the controller 410. In certain implementations, the controller 410 can further include a demultiplexer, deserializer or other device or component for separating the image data from each of the image sensors so that the image frames can be processed in parallel by the controller.

In one embodiment, the field-of-view being imaged by an FPRI system is divided into smaller regions or tiles. The FPRI system can include parallel processing capabilities to process multiple tiles in parallel. For example, the FPRI system 400 may process raw images of each tile to reconstruct phase and amplitude data for multiple tiles in parallel. The FPRI system 400 may also process raw images of each tile to generate an aberration-free image for multiple tiles in parallel.

In one embodiment, the FPRI system 100 shown in FIG. 1 further comprises all the components of the FPRI system 200 shown in FIG. 2 where the components of the FPRI system 200 are enclosed within the casing 110 shown in FIG. 1.

In one embodiment, the FPRI system 200 shown in FIG. 2 further comprises one or more components (e.g., the controller 410) of the FPRI system 440 shown in FIG. 4. For example, the FPRI system 200 may include the controller 410 in communication with the illumination source 210, the aperture modulator 240, and the imaging system 250, the communication 412, the display 414, and the internal memory 420.

III. FPRI Methods

Conventional retinal imaging methods physically characterize the inherent optical aberrations of the eye and modulate the imaging system to correct for these aberrations during examination of the eye. With these conventional systems, a patient needs to be under examination during the aberration characterization process and during a subsequent image acquisition procedure, which can uncomfortably extend the length of time the patient needs to be under examination. The FPRI methods and systems described herein use a significantly different strategy for achieving high-resolution aberration corrected retinal images. The FRPI methods collect a sequence of raw retinal images in which optical aberrations are present, and then computationally determine the aberrations of the eye and titrate the raw images into a high-resolution substantially aberration-free retinal image. When using systems that implement FPRI methods, the patient need only be present during the raw image acquisition procedure.

The FPRI methods include operations that produce, a substantially aberration-free image of the retina. In these FPRI methods, a sequence of raw retinal images is captured within a relatively short time frame since the eye being examines tends to move. In one embodiment, a sequence of raw retinal images is captured in less than 0.025 seconds. In one embodiment, a sequence of raw retinal images is captured in less than 0.05 seconds. In one embodiment, a sequence of raw retinal images is captured in less than 0.1 seconds. In another embodiment, a sequence of raw retinal images is captured in less than 0.5 seconds. In another embodiment, a sequence of raw retinal images is captured in less than 0.25 seconds. In another embodiment, a sequence of raw retinal images is captured in less than 0.1 seconds. In another embodiment, a sequence of raw retinal images is captured in less than 1 second.

In some embodiments, the person whose eye is being examined must be positioned during both focusing on the retina and the subsequent acquisition of the sequence of raw retinal images. In one case, the focusing and acquisition of the sequence takes less than 10 seconds. In another case, the focusing and acquisition of the sequence takes less than 30 seconds. In another case, the focusing and acquisition of the sequence takes less than 1 minute.

The imaging system captures the sequence of raw images while the retina is illuminated and while an aperture is shifting to different locations at the Fourier plane of the approximate retinal plane using an aperture modulator (e.g., SLM). The raw images are stitched together with an improved FP-based technique to generate a high-resolution, complex retinal image and also to determine the optical aberrations of the eye. The aberrations are then separated from the retinal image computationally by simulated annealing.

Figure 5:
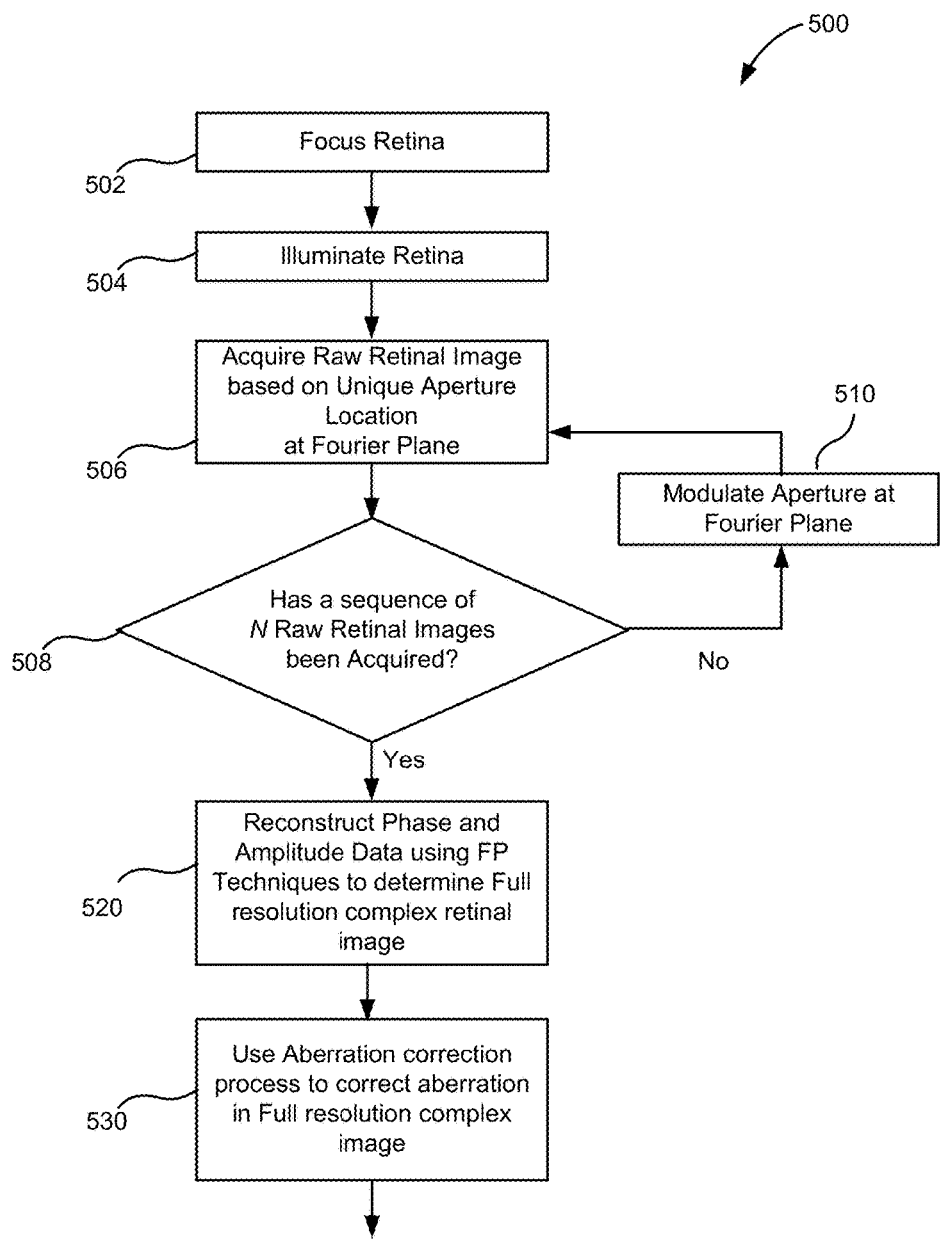
FIG. 5 is a flowchart of operations of an FPRI method that can be implemented by an FPRI system, according to embodiments.

FIG. 5 is a flowchart of operations of an FPRI method that can be implemented by an FPRI system, according to embodiments. At operation 502, the FPRI system is focused at the approximate plane of the retinal layer at the back of the eye being examined. This first operation may involve, for example, locating the eye (e.g., by placing person's head on a stationary neck rest) such that the retina is in focus. In addition or alternatively, the optical system of the FPRI system may include components that focus on the retina of the eye. For example, a focusing lens may be used to focus on the retinal layer.

At operation 504, the retina is illuminated by plane wave illumination. For example, the illumination source, such as an LED, may be activated (e.g., turned on) to provide plane wave illumination which is propagated via the optical system to the eye. In one embodiment, the illumination source provides pulses of light to help reduce motion artifacts during raw image acquisition. For example, pulses with pulse duration having a value in a range of between about 0.05 and about 0.15 may be used. In one case, pulses with a pulse duration of about 0.1 ms are used. In another case, pulses with a pulse duration of about 0.05 ms are used. In another case, pulses with a pulse duration of about 0.2 ms are used. In another case, pulses with a pulse duration of about 0.15 ms are used. In one embodiment, a beamsplitter is placed in front of the eye to allow an illumination source, e.g. an LED, to illuminate the eye with a sequence of pulsed light.

At operation 506, one or more image sensors acquires a raw retinal image while an aperture modulator generates an aperture at a unique location of the Fourier plane. The aperture blocks the light entering into the pupil plane of the imaging system so that the image sensor(s) captures an intensity distribution with image data associated with the unique location of the aperture at the Fourier plane.

At operation 508, the processor(s) executes instructions stored on memory to determine whether a sequence of N raw retinal images has been acquired. If the processor(s) determine that the N raw retinal images have not been acquired, the processor(s) send control instructions to the aperture modulator to modulate the aperture to incrementally shift it to another unique position at the Fourier plane (operation 510).

The operations 504, 506, 508, and 510 are generally referred to as the image acquisition process of the FPRI method. During iterated operations 506, 508, and 510, the optical system of the FPRI system propagates light reflected from the plane-wave illuminated retina to the imaging system while an aperture modulator (e.g. SLM) modulates an admittance circular pupil function (also referred to herein as a "window" or as an "aperture" and sometimes as a "sub-aperture") to shift it to unique locations at the Fourier plane of the approximate retinal plane with the cones and rods visible. One or more processors (e.g., of a controller) sends control signals to the illumination source, the aperture modulator, and the imaging system to synchronize capturing of a sequence of raw retinal images while the aperture modulator generates apertures at different locations at the Fourier plane and while the illumination source provides plane wave illumination. In some cases, the illumination source provides pulses of light to help reduce motion artifacts during the raw image acquisition procedure. In these cases, the imaging system (e.g., high-speed digital camera) is synchronized so that the exposure times for capturing the raw images coincide with the duration of the pulses. With this synchronization acquisition process, the imaging system can capture each raw retinal image of the sequence while the aperture is at a unique location at the Fourier plane.

During the image acquisition process, the aperture modulator sequentially translated the aperture (also called a sub-aperture or window herein) to different locations across the Fourier plane of the approximate retinal plane. The aperture modulator typically shifts the aperture in the Fourier plane to cover the entire area defined by the pupil function. The aperture is a window function, $W_j(k_x, k_y)$, located on the Fourier plane that transmits the part of light incident inside the shape while blocking the part incident outside of the shape. The aperture shape is typically smaller than the dimension of the first collection lens pupil at the Fourier plane. The aperture blocks and only transmits a small portion of the light entering into the pupil plane of the imaging system. Although the aperture is described in this section as circular, other shapes may be used such as rectangular, triangular, etc. In one case, the aperture is a circle of 1 mm in diameter. The aperture modulator sequentially translates the aperture in step increments in a pattern with unique aperture locations, for example, a square grid pattern. In one case, for example, aperture modulator generates a 1 mm diameter admittance circular pupil function and sequentially translates it in step increments of 0.3254 mm in a square grid pattern. Other diameters, step increments and patterns may be used. Generally the adjacent aperture regions in the Fourier plane overlap by at least 60% in some cases, at least 65% in other cases, at least 70% in other cases, or at least 75% in other cases. The grid pattern followed by the aperture modulator has N aperture locations. In one case, the number of unique aperture locations N is about 200. In one case, the number of aperture locations N is in a range of 1 to about 2000. In another case, the number of aperture locations N is in the range of 1 to about 200. In another case, the number of aperture locations N is in the range of 1 to about 3000. In another case, the number of aperture locations N is in the range of 200 to 1000. In one embodiment, the aperture modulator is configured to shift the aperture to N different locations in less than about 1 second. In one embodiment, the aperture modulator is configured to shift the aperture to N different locations in 0.5 seconds. In one case, the aperture modulator is configured to shift the aperture to N different locations in 0.1 seconds. The duration of the image acquisition process is typically less than 1 second. In one case, the duration may be less than 0.5 seconds.

If the processor(s) determine that the N raw retinal images have been acquired at operation 508, the processor(s) execute instructions stored on memory to determine the phase and amplitude data from the sequence of N raw retinal images using an improved FP technique and then determining the full resolution complex retinal image based on the phase and amplitude data at operation 520. Each raw retinal image acquired by the imaging system during the image acquisition process is a unique, poorly resolved measurement of the retinal surface. Both the inherent optical aberrations of the eye, as well as the finite passband of the shifting aperture, limit their achievable resolution.

In one embodiment, when the processor(s) determines that the N raw retinal images have been acquired at operation 508, the one or more processors (e.g., of a controller) send control signals to the illumination source, the aperture modulator, and the imaging system to stop the image acquisition. At this point, these different components (e.g., illumination source) can be powered down and the person whose retina is being imaged does not need to be positioned in front of the FPRI system.

At operation 520, the processor(s) executes instructions stored on memory to run operations of an improved FP technique to extract both phase and amplitude information of the wavefront emerging from the eye. During this operation 520, the acquired sequence of raw retinal images are fused into a full-resolution complex image. The image is a combination of the phase aberration from the eye and the imaging system and the complex sample distribution of the retinal layer of interest.

At operation 530, the processor(s) executes instructions stored on memory to run an aberration correction process to determine the aberration of the eye and remove the aberration from the complex retinal image to generate a substantially aberration-free retinal image. In one example, the aberration correction process includes an annealing procedure that is applied on the complex image to separate the retinal image and the optical aberrations of the eye by modeling the aberrations as a combination of Zernike polynomials. By defining a metric for quantifying a sharply focused image, the correction procedure generates various combinations of the Zernike aberration modes and applies them to the reconstructed image, computes the metric's value for each simulated image, and finds the optimum combination, which is equivalent to the correct model for the aberrations in the reconstructed image. An aberration-free retinal imaging is produced as a result. Details of an example of an annealing procedure can be found in R. Horstmeyer, X. Ou, J. Chung, G. Zheng and C. Yang, "Overlapped Fourier coding for optical aberration removal," Optics Express, 2014, which is hereby incorporated by reference in its entirety.

Figure 6A:
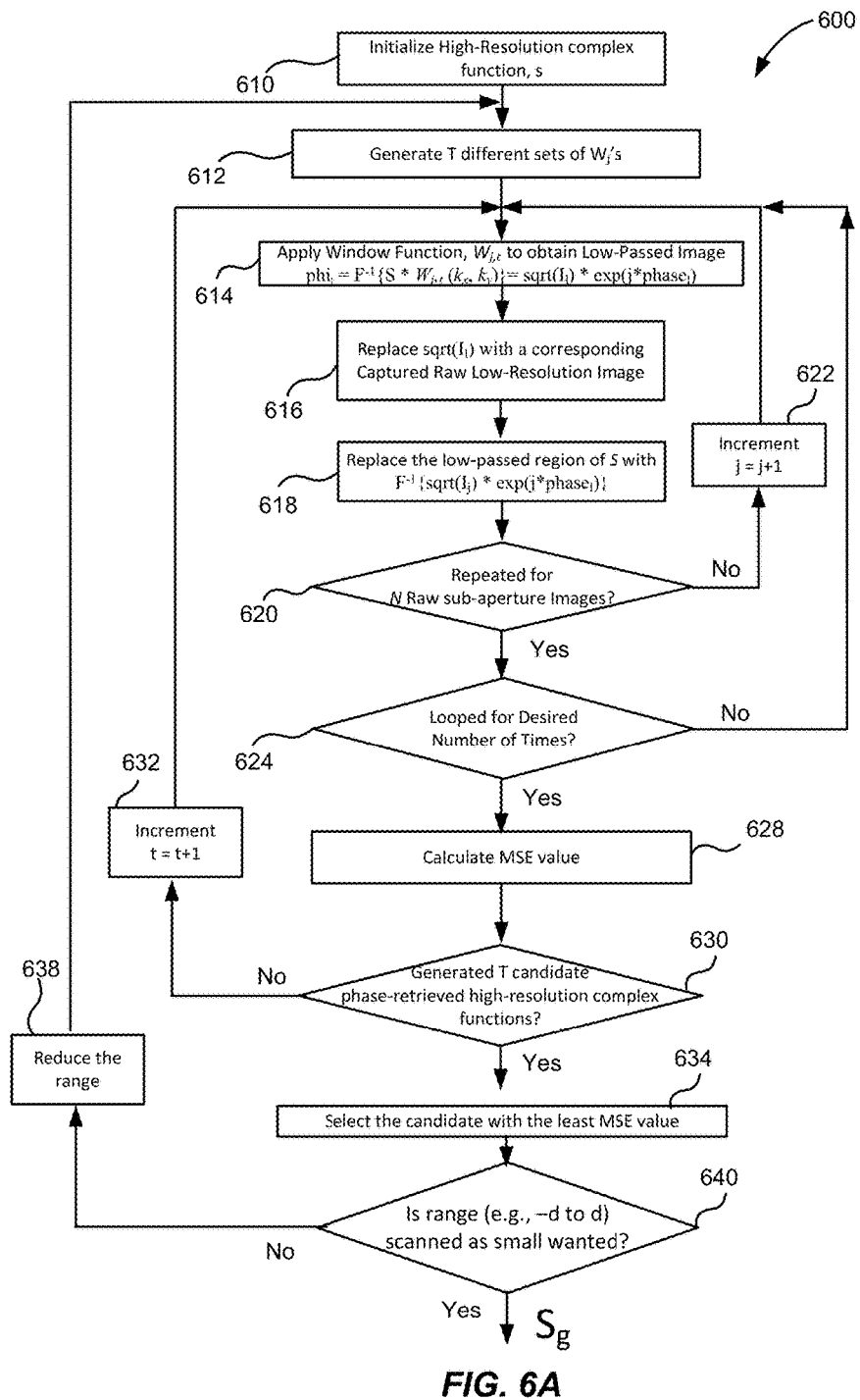
FIG. 6A is a flowchart of a first part of the simulated annealing procedure called the geometric distortion part, according to an embodiment.
Figure 6B:
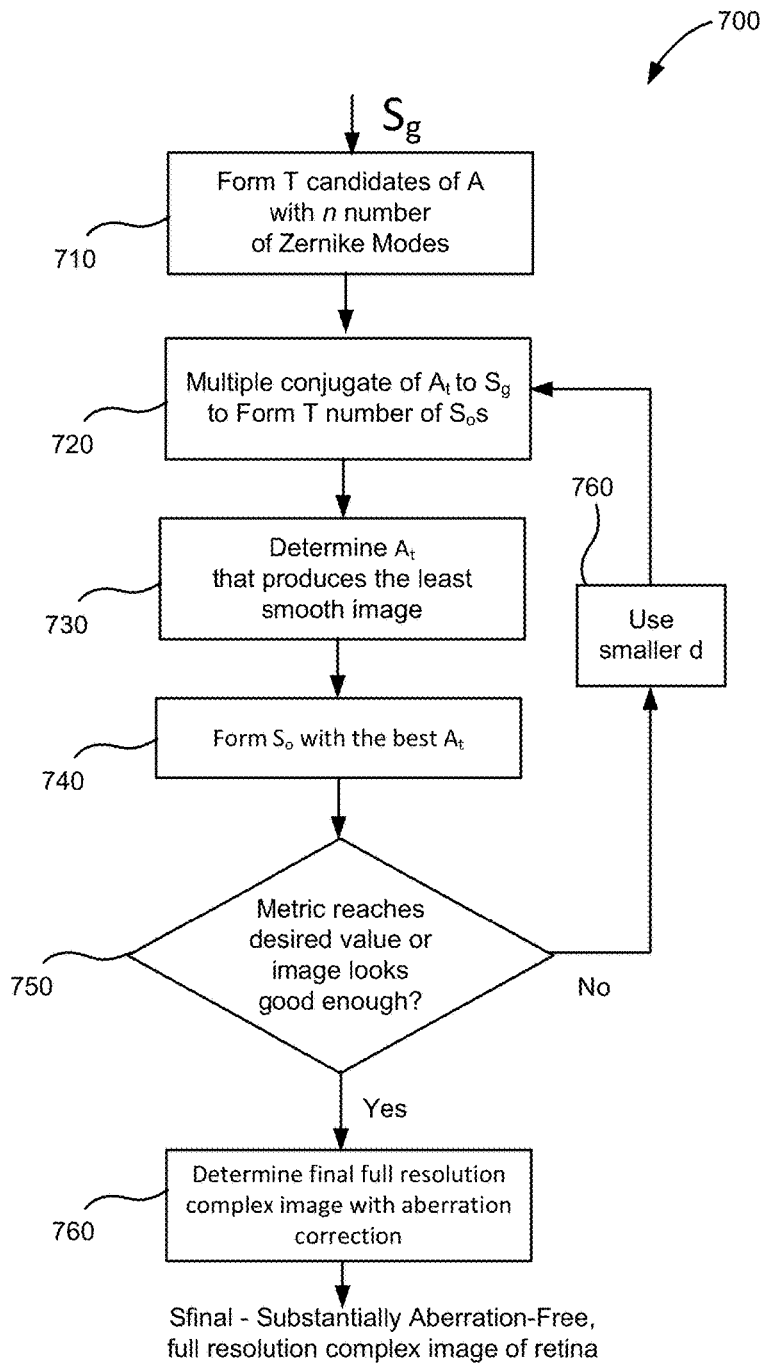
FIG. 6B is a flowchart of a second part of the simulated annealing procedure called the phase aberration part, according to an embodiment

An example of sub-operations of an embodiment of operations 520 and 530 using a simulated annealing procedure is described in detail in FIG. 6A and FIG. 6B. FIG. 6A is a flowchart of a first part of the simulated annealing procedure called the geometric distortion part, according to an embodiment. Details of an example of a simulated annealing process can be found in Roarke Horstmeyer, Xiaoze Ou, Jaebum Chung, Guoan Zheng, and Changhuei Yang, "Overlapped Fourier coding for optical aberration removal," Optics Express, vol. 22, no. 20, (Oct. 6, 2014), which is hereby incorporated by reference in its entirety.

At operation 610, the full resolution complex function of the sample, $s=\text{sqrt}(I_h)*\exp(j*\text{phase}_h)$, is initialized in the spatial domain, with its Fourier spectrum represented by $S=F\{s\}$. For example, the full resolution complex function in the spatial domain, $\text{sqrt}(I_h)*\exp(j*\text{phase}_h)$, may be set to 1: $\text{sqrt}(I_h)*\exp(j*\text{phase}_h)=1$. As another example, the full resolution complex function in the Fourier domain, $\text{sqrt}(I_h)*\exp(j*\text{phase}_h)$, may be set to the square root of the first raw retinal intensity: $\text{sqrt}(I_h)*\exp(j*\text{phase}_h)=\text{sqrt}(I_1)$. The window functions, $W_j$'s, representing the sub-apertures used to capture the raw images, are also initialized. For example, $W_j$'s are rectangular apertures shifted in a square grid pattern. In addition, the various loop index variables are initialized. For example, the inner loop index variable, j, is set to 1 (first iteration) and the outer loop variable, t, is set to 1. The outer loop index variable, t, is the index incrementing the set of window functions for all raw images and the inner loop index variable, j, is the index incrementing the raw images.

At operation 612, T different sets of window functions for all raw images, $W_j$'s, are generated. These $W_j$'s are generated by geometrically shifting, by different discrete values in the range of −d to d, from the initial guesses from operation 610. For example, for a pupil plane of 10 mm by 10 mm and contiguous $W_j$'s separated by 1 mm measured from their centers, d may be 0.1 mm and each $W_j$ may be shifted in x and y by any discretized steps between −0.1 mm and 0.1 mm (e.g. −0.05 mm, 0 mm, or 0.05 mm).

At operation 614, the window function, $W_{j,t}(k_x, k_y)$ is applied in the sample's Fourier spectrum to obtain a low-passed image i.e. $F^{-1}\{S*W_{j,t}(k_x, k_y)\}=\text{sqrt}(I_l)*\exp(j*\text{phase}_l)$.

At operation 616, $\text{sqrt}(I_l)$ from 614 is replaced with a corresponding captured raw retinal image, $\text{sqrt}(I_j)$ i.e. $\text{sqrt}(I_l)*\exp(j*\text{phase}_l) => \text{sqrt}(I_j)*\exp(j*\text{phase}_l)$.

At operation 618, replace the low-passed region of S with $F^{-1}\{\text{sqrt}(I_j)*\exp(j*\text{phase}_l)\}$. S is the high resolution image in the Fourier domain being reconstructed.

At operation 620, it is determined whether the operations of 614, 616, and 618 have been repeated for all the N raw sub-aperture retinal images, i.e. all the $W_{j,t}$s. The $W_{j,t}$s are the same window function shifted to different regions of the $k_x$ $k_y$ domain. If it is determined that the operations of 614, 616, and 618 have not been repeated for all the N raw sub-aperture retinal images, then j is incremented (j=j+1) at operation 622 and operations 614, 616, and 618 are repeated for the window function at the next raw image.

If, at operation 620, it is determined that the operations of 614, 616, and 618 have been repeated for all the N raw sub-aperture retinal images, then it is determined whether the operations 614, 616, and 618 have been looped for the desired number of times (operation 624). This loop is for convergence of the phase retrieval process. If it is determined, at operation 624, that the operations 614, 616, and 618 have not been looped for the desired number of times, then the method returns to operation 614.

If, at operation 624, it is determined that the operations 614, 616, and 618 have been looped for the desired number of times, then the MSE value is calculated at operation 628. At operation 628, the MSE value is calculated by simulating a low-resolution image capturing process and comparing the resulting simulated images to the measured images. For a $t^{th}$ set, the $MSE_t=\Sigma_j\Sigma_x\Sigma_y(|\varphi_j'(x,y)|I_j(x,y))^2$, where $\varphi_j'(x,y)= F^{-1}\{S*W_{j,t}(k_x+dx_{j,t},k_y+dy_{j,t})\}$.

At operation 630, it is determined whether T candidate phase-retrieved high-resolution complex functions have been generated. Each candidate phase-retrieved high-resolution complex function is generated by $W_j$s that are geometrically shifted by different discrete values within the range −d to d, resulting in $W_{j,t}(k_x+dx_{j,t},k_y+dy_{j,t})$ where $dx_{j,t}$ and $dy_{j,t}$ are some discrete steps between −d and d. If it is determined that less than T candidate phase-retrieved high-resolution complex functions have been generated at operation 630, then t is incremented (t=t+1) at operation 632 and the method returns to operation 614. For each the T sets incremented at operation 632, an MSE value is calculated at operation 628.

At operation 634, the candidate phase-retrieved high-resolution complex function with the lowest calculated MSE value is selected. The candidate, $W_{j,t}$, related to this lowest calculated MSE value is the correct guess for the locations of the sub-apertures used to capture the raw retinal images. The S reconstructed is the sample image with geometric distortion corrected for.

At operation 636, it is determined whether the range (e.g., range from −d to d) scanned is as small as wanted. If it is determined that the range is not as small as wanted, then the range is reduced (e.g., reducing d) at operation 638 and the method returns to operation 612. For example, if d was 0.1 mm, it may be reduced to 0.05 mm or even 0.01 mm. If we want the final range of uncertainty for the windows' location to be less than 0.01 mm, the method should return to operation 612 until the scanning range is less than −0.01 mm to 0.01 mm. It may be determined that the range is small enough, for example, if the MSE is below some desired value or when the looks good enough. If visual qualification is difficult, then the amount of improvement in the MSE value at the end of the procedure may be used to decide if the MSE value remains unchanged or only changed negligibly and obviate the need to decrease the range. The negligible MSE change may be less than 1% in one example, 0.1% in another example, or 0.01% in another example. If it is determined that the range is as small as wanted at operation 636, then the sample spectrum with geometric distortion corrected, $S_g$, is outputted.

FIG. 6B is a flowchart of a second part of the simulated annealing procedure called the phase aberration part, according to an embodiment. This phase aberration starts at operation 710 with the sample spectrum with geometric distortion corrected, $S_g$, output from operation 636 shown in FIG. 6A. $S_g=S_o*A$ where $S_o$ is the sample-only spectrum and A is the pupil function of the imaging system which contains the wavefront aberration (phase aberration).

At operation 710, T candidates of A are formed. The T candidates of A are formed with n number of Zernike modes of aberrations. Each mode's coefficient is able to vary from −d to d in discrete steps (e.g. 5 evenly-spaced values between −d and d). For example, if A only has one Zernike mode, e.g. defocus, then the $t^{th}$ candidate for A would be $A_t = A_0 * e^{(i\Delta_t(k_x^2 + k_y^2))}$ where $\Delta_t$ is the coefficient value $d_t$ and $A_0$ is the initial aberration function (e.g., 1 in the first iteration).

At operation 720, the conjugate of $A_t$ to $S_g$ is multiplied to form T number of $S_o$s (i.e. $S_{o,t} = A_t^{**} S_g$).

At operation 730, determine the best $A_t$ that produces the least smooth image. In one case, the smoothness of the phase variation of $S_{o,t}$, with the $A_t$ that produces the least smooth phase is determined. In another case, the smoothness in the inverse Fourier transform of $S_{o,t}$, with $A_t$ producing the least smooth image is determined. The $A_t$ that produces the least smooth image most accurately describes the aberration of the eye. An example of the metric to determine smoothness is taking the second derivative of the image and observing the highest modulus value.

At operation 740, form $S_o$ with the best $A_t$ determined in operation 730 by updating $A_o$ with the best $A_t$. That is, update $A_o = A_t$.

At operation 750, it is determined whether a metric reaches the desired value or the image looks good enough. The second derivative of the image may be used to quantify the smoothness, for example, and one can determine whether the smoothness value is stagnating after some number of loops. If it is determined that that neither the metric reaches the desired value nor the image looks good enough, then a smaller d is used at operation 760 and the method returns to operation 720. d may be decremented by 50% in one example or 90% in another.

If it is determined that either the metric reaches the desired value or the image looks good enough, then the method determines the final full resolution, complex image with aberration correction, $S_{final}$, at operation (operation 760). The final image with aberration correction is obtained by $S_{final} = S_g * A_t^*$ and inverse Fourier transformation. The aberration of the retina is $A_t$ for phase aberration and the grid pattern generated by the locations of the $W_{j,t}$'s for geometric distortion.

Modifications, additions, or omissions may be made to any of the above-described embodiments without departing from the scope of the disclosure. Any of the embodiments described above may include more, fewer, or other features without departing from the scope of the disclosure. Additionally, the steps of the described features may be performed in any suitable order without departing from the scope of the disclosure.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a CRM such as a random access memory (RAM), a read only memory (ROM), a magnetic medium such as a hard-drive or a floppy disk, or an optical medium such as a CD-ROM. Any such CRM may reside on or within a single computational apparatus, and may be present on or within different computational apparatuses within a system or network.

Although the foregoing disclosed embodiments have been described in some detail to facilitate understanding, the described embodiments are to be considered illustrative and not limiting. It will be apparent to one of ordinary skill in the art that certain changes and modifications can be practiced within the scope of the appended claims.

One or more features from any embodiment may be combined with one or more features of any other embodiment without departing from the scope of the disclosure. Further, modifications, additions, or omissions may be made to any embodiment without departing from the scope of the disclosure. The components of any embodiment may be integrated or separated according to particular needs without departing from the scope of the disclosure.

What is claimed is:

1. A Fourier ptychographic retinal imaging method, the method comprising:
   focusing on a retina of an eye, wherein focusing on the retina comprises moving one or both of the eye and a focusing lens to provide an optical path between the retina and the focusing lens that is approximately a sum of a focal length of the eye and a focal length of the focusing lens;
   illuminating the eye with plane wave illumination;
   acquiring, using one or more image sensors, a sequence of raw retinal images based on light reflected from the retina, wherein the sequence of raw retinal images is acquired while light reflected from the retina is passed by an aperture to the one or more image sensors as the aperture is sequentially shifted to different locations at the Fourier plane of an approximate plane of the retina, wherein the sequence of raw retinal images corresponds to regions in Fourier space;
   after acquiring the raw retinal images, reconstructing a complex full resolution image of the retina with phase image data recovered by iteratively updating regions in Fourier space with data from the plurality of raw retinal images; and
   correcting aberration in the reconstructed complex full resolution image of the retina to generate a substantially aberration-free, full resolution retinal image.

2. The Fourier ptychographic retinal imaging method of claim 1, wherein correcting aberration comprises using an annealing procedure.

3. The Fourier ptychographic retinal imaging method of claim 1, wherein illuminating the retina with plane wave comprises illuminating the retina with pulses of monochromatic light.

4. The Fourier ptychographic retinal imaging method of claim 3, further comprising synchronizing the timing of the pulses of monochromatic light with sampling times for acquiring the sequence of raw retinal images and modulation of the apertures to different locations at the Fourier plane.

5. The Fourier ptychographic retinal imaging method of claim 3, further comprising receiving control signals at an aperture modulator, the one or more image sensors and an illumination source, wherein the received control signals synchronize the timing of the pulses of monochromatic light from the illumination source with the exposure times for acquiring the sequence of raw retinal images by the one or more image sensors and with the locating of the apertures at different locations at the Fourier plane by the aperture modulator.

6. A Fourier ptychographic retinal imaging method, the method comprising:
   receiving a sequence of raw retinal images of a retina of an eye from an imaging system, wherein the sequence of raw retinal images is acquired by one or more image sensors of the imaging system, wherein the sequence of raw retinal images is based on light reflected from the retina while an aperture modulator sequentially shifts an aperture to different locations at the Fourier plane of an approximate plane of the retina and while an illumination source provides plane wave illumination propagated to the eye through an optical system;

reconstructing a complex full resolution image of the retina with phase and amplitude image data recovered by iteratively updating regions in Fourier space with data from the plurality of raw retinal images; and correcting aberration in the reconstructed complex full resolution image of the retina to generate a substantially aberration-free, full resolution retinal image.

7. The Fourier ptychographic retinal imaging method of claim 6, wherein correcting aberration comprises executing instructions to use operations of an annealing process.

8. The Fourier ptychographic retinal imaging method of claim 7, further comprising sending control signals to the imaging system, the aperture modulator, and the illumination source, wherein the control signals synchronize illumination provided by the illumination system with sampling times of the imaging system and with different locations of the aperture at the Fourier plane modulated by the aperture modulator.

9. A Fourier ptychographic retinal imaging system for imaging a retina of an eye, the system comprising:
   an illumination source configured to provide plane wave illumination;
   an aperture modulator configured to sequentially shift an aperture to different locations at the Fourier plane of an approximated plane of the retina;
   an imaging system with one or more image sensors configured to acquire a sequence of raw retinal images based on light reflected from the retina;
   an optical system for propagating the plane wave illumination to the eye and for propagating light reflected from the retina to the imaging system; and
   a processor in communication with the imaging system to receive a signal with image data comprising the sequence of raw retinal images, the processor configured to execute instructions for reconstructing a complex full resolution image of the retina with phase and amplitude image data recovered by iteratively updating regions in Fourier space with data from the plurality of raw retinal images, wherein the processor is further configured to execute instructions for correcting aberration in the complex full resolution image to generate a substantially aberration-free, full resolution image of the retina.

10. The Fourier ptychographic retinal imaging system of claim 9, wherein the illumination source is configured to provide pulses of plane wave illumination, wherein the pulses are synchronized with sampling times of the imaging system and time for modulating the aperture to different locations at the Fourier plane.

11. The Fourier ptychographic retinal imaging system of claim 10, wherein the illumination source monochromatic light.

12. The Fourier ptychographic retinal imaging system of claim 9, wherein the instructions for correcting aberration includes instructions for using an annealing procedure.

13. The Fourier ptychographic retinal imaging system of claim 9, wherein the aperture modulator provides neighboring apertures that overlap by at least 60%.

14. The Fourier ptychographic retinal imaging system of claim 9, wherein the aperture modulator provides neighboring apertures that overlap by at least 70%.

15. The Fourier ptychographic retinal imaging system of claim 9, wherein the aperture modulator is a spatial light modulator configured to digitally address to shift the aperture to the different locations across the Fourier plane.

16. The Fourier ptychographic retinal imaging system of claim 9, wherein the aperture modulator is a digital micromirror device.

17. The Fourier ptychographic retinal imaging system of claim 9, wherein the imaging system is a high speed digital camera.

18. The Fourier ptychographic retinal imaging system of claim 9, wherein the imaging system configured to acquire images in a range of about 200 frames per second to 500 frames per second.

19. The Fourier ptychographic retinal imaging system of claim 9, wherein the optical system comprises a first polarizing beam splitter for reflecting plane wave illumination received from the illumination source toward the eye.

20. The Fourier ptychographic retinal imaging system of claim 9, wherein the sequence of images acquired has a number in the range of 200 to 500, wherein the images are acquired in less than about 0.5 seconds.

21. The Fourier ptychographic retinal imaging system of claim 9, wherein the sequence of images acquired has a number in the range of 200 to 500, wherein the images are acquired in less than about 1.0 second.

* * * * *